(12) United States Patent
Wada et al.

(10) Patent No.: US 11,542,292 B2
(45) Date of Patent: Jan. 3, 2023

(54) POLYMERIZABLE COMPOUND, COMPOUND, AND METHOD FOR PRODUCING BORANOPHOSPHATE OLIGOMER

(71) Applicant: TOKYO UNIVERSITY OF SCIENCE FOUNDATION, Tokyo (JP)

(72) Inventors: Takeshi Wada, Tokyo (JP); Tatsuya Saito, Tokyo (JP); Yuka Ishii, Tokyo (JP); Yohei Nukaga, Tokyo (JP)

(73) Assignee: TOKYO UNIVERSITY OF SCIENCE FOUNDATION, Tokyo (JP)

( * ) Notice: Subject to any disclaimer, the term of this patent is extended or adjusted under 35 U.S.C. 154(b) by 851 days.

(21) Appl. No.: 16/349,438

(22) PCT Filed: Nov. 9, 2017

(86) PCT No.: PCT/JP2017/040469
§ 371 (c)(1),
(2) Date: May 13, 2019

(87) PCT Pub. No.: WO2018/088491
PCT Pub. Date: May 17, 2018

(65) Prior Publication Data
US 2019/0270765 A1    Sep. 5, 2019

(30) Foreign Application Priority Data
Nov. 14, 2016  (JP) .............................. JP2016-221656

(51) Int. Cl.
| | | |
|---|---|---|
| C07H 19/073 | (2006.01) |
| C07H 19/173 | (2006.01) |
| C07H 21/00  | (2006.01) |
| C07F 5/02   | (2006.01) |
| C07F 9/6584 | (2006.01) |
| C07F 9/6558 | (2006.01) |
| C12N 15/113 | (2010.01) |

(52) U.S. Cl.
CPC ............ *C07H 19/173* (2013.01); *C07F 5/02* (2013.01); *C07F 9/6558* (2013.01); *C07F 9/6584* (2013.01); *C07H 19/073* (2013.01); *C07H 21/00* (2013.01); *C12N 15/113* (2013.01); *C12N 2310/11* (2013.01); *C12N 2310/31* (2013.01); *C12N 2310/321* (2013.01); *Y02P 20/55* (2015.11)

(58) Field of Classification Search
None
See application file for complete search history.

(56) References Cited

U.S. PATENT DOCUMENTS

| | | | | |
|---|---|---|---|---|
| 8,859,755 B2 * | 10/2014 | Wada | ...................... | C07H 19/06 536/25.33 |
| 2011/0294124 A1 | 12/2011 | Wada et al. | | |
| 2013/0184450 A1 | 7/2013 | Wada et al. | | |

FOREIGN PATENT DOCUMENTS

| | | | |
|---|---|---|---|
| JP | 2012-510460 A | 5/2012 | |
| JP | 5847700 B2 | 1/2016 | |
| WO | WO-2010/064146 A2 | 6/2010 | |
| WO | WO-2016/079181 A1 | 5/2016 | |
| WO | WO-2016079181 A1 * | 5/2016 | ............. C07H 21/00 |

OTHER PUBLICATIONS

Partial European Search Report in EP Application No. 21170140.4 dated Aug. 20, 2021, 18 pages.
Office Action in Japanese Patent Application No. 2018-550265 dated Sep. 21, 2021, 8 pages.
Nukaga et al., "Stereocontrolled Solid-Phase Synthesis of Phosphate/Phosphorothioate (PO/PS) Chimeric Oligodeoxyribonucleotides on an Automated Synthesizer Using an Oxazaphospholidine-Phosphoramidite Method", J Org Chem, 2016, vol. 81, pp. 2753-2762.
Oka et al., "Solid-phase synthesis of stereoregular oligodeoxyribonucleoside phosphorothioates using bicyclic oxazaphospholidine derivatives as monomer units", J Am Chem Soc, 2008, vol. 130, pp. 16031-16037.
Sood et al. "Boron-Containing Nucleic Acids. 2. Synthesis of Oligodeoxynucleoside Boranophosphates", J. Am. Chem. Soc. 112, 1990, pp. 9000-9001.
Zhang et al., "Synthesis and Hybridization Study of a Boranophosphate-Linked Oligothymidine Deoxynucleotide", Tetrahedron Letters, vol. 38, No. 28, 1997, pp. 4957-4960.
Sergueev et al., "H-Phosphonate Approach for Solid-Phase Synthesis of Oligodeoxyribonucleoside Boranophosphates and Their Characterization", J. Am. Chem. Soc., 120, 1998, pp. 9417-9427.
Higson et al., "Synthesis of an Oligothymidylate Containing Boranophosphate Linkages", Tetrahedron Letters 39, 1998, pp. 3899-3902.
Iwamoto et al., "Stereocontrolled Solid-Phase Synthesis of Oligonucleoside H-Phosphonates by an Oxazaphospholidine Approach", Angew. Chem. Int. Ed. 48, 2009, pp. 496-499.
Nukaga et al., "Enhancement of the Affinity of 2' O-Me-oligonucleotides for Complementary RNA by Incorporating a Stereoregulated Boranophosphate Backbone", T.RSC Adv. 5, 2015, pp. 2392-2395.

(Continued)

*Primary Examiner* — Traviss C McIntosh, III
(74) *Attorney, Agent, or Firm* — Marshall, Gerstein & Borun LLP

(57) ABSTRACT

Provided a polymerizable compound represented by the following Formula A-1 or Formula A-2: In Formula A-1 or Formula A-2, $R^1$ represents an electron-donating group; n represents an integer from 1 to 5; $R^2$ represents a hydrogen atom, a halogen atom, or $-OR^O$, wherein $R^O$ represents a hydrogen atom, an alkyl group, or a protecting group of a hydroxy group; $R^3$ represents a hydrogen atom or a protecting group of a hydroxy group; and X represents a structure represented by any one of Formula B-1 to Formula B-5.

4 Claims, 3 Drawing Sheets

(56) References Cited

OTHER PUBLICATIONS

Iwamoto et al., "Stereocontrolled Synthesis of Oligodeoxyribonucleoside Boranophosphates by an Oxazaphospholidine Approach Using Acid-labile N-protecting Groups", Tetrahedron Letters 53, 2012, pp. 4361-4364.
Saito et al., "Stereocontrolled Synthesis of Boranophosphate DNA by an Oxazaphospholidine Approach", The Proceeding of The Chemical Society of Japan Annual Meeting in Spring, vol. 97, 4C2-10, Mar. 3, 2017, 1 page.
Search Report and Written Opinion in International Application No. PCT/JP2017/040469 dated Jan. 30, 2018, 7 pages.

* cited by examiner (A) crude (Rp)-T₅T [entry 1, (Rp)-24a]        (B) crude (Sp)-T₅T [entry 6, (Sp)-24a]

(C) crude (Rp)-dC₅T [entry 2, (Rp)-24b]        (D) crude (Sp)-dC₅T [entry 7, (Sp)-24b]

(E) crude (Rp)-dA₅T [entry 3, (Rp)-24c]        (F) crude (Sp)-dA₅T [entry 8, (Sp)-24c]

POLYMERIZABLE COMPOUND, COMPOUND, AND METHOD FOR PRODUCING BORANOPHOSPHATE OLIGOMER

TECHNICAL FIELD

The present disclosure relates to a polymerizable compound, a compound, and a method of producing a boranophosphate oligomer.

BACKGROUND ART

An antisense molecule having a complementary base sequence to a target nucleic acid forms a duplex with the target nucleic acid and protein production from the target nucleic acid can be inhibited. The antisense molecule receives attention as an effective medicine for gene treatment, since the antisense molecule directly act on a disease related gene, when the disease-related gene is selected as the target nucleic acid.

The antisense molecule (nucleic acid oligomer) is mainly required to have cell membrane permeability, nuclease resistance, chemical stability in the body (for example, under the environment of pH 7.4), and a property of forming stable duplex with a specific base sequence, from the viewpoint of effectively inhibiting production of target protein.

As the antisense molecule, for example, an oligomer having a structure in which at least a portion is substituted by a phosphorothioate bond among phosphodiester structures of nucleic acid oligomers, an oligomer having a structure in which at least a portion is substituted by a boranophosphate structure (hereinafter, referred to as "boranophosphate oligomer") among phosphodiester structures of nucleic acid oligomers, and the like are known, and there have been many extensive research examples so far and the oligomers have been put to practical use even as medicine.

The boranophosphate structure refers to a structure in which one of non-bridging oxygen atoms in a phosphodiester structure is substituted by a borano group (—$BH_3$).

The boranophosphate oligomer has advantages of having high nuclease resistance, high RNA interference (RNAi) activity, higher affinity for RNA than DNA, a low nonspecific interaction with proteins, and applicability to boron neutron capture therapy (BNCT).

A conventional method of producing a boranophosphate oligomer may include methods described in J. Am. Chem. Soc. 1990, 112, 9000, Tetrahedron Lett. 1997, 38, 4957, J. Am. Chem. Soc. 1998, 120, 9417, Tetrahedron Lett. 1998, 39, 3899, T. Angew. Chem. Int. Ed. 2009, 48, 496-499, T. RSC Adv. 2015, 5, 2392-2395, and Tetrahedron Lett. 2012, 53, 4361-4364.

SUMMARY OF INVENTION

Since in a boranophosphate oligomer, a phosphorus atom is an asymmetric center, the boranophosphate oligomer contains monomer units which are two kinds of stereoisomers (Rp isomer, Sp isomer) having different properties from each other.

Thus, development of a method of stereoselectively synthesizing the isomers is required.

In a method of synthesizing a boranophosphate oligomer described in J. Am. Chem. Soc. 1990, 112, 9000, Tetrahedron Lett. 1997, 38, 4957, J. Am. Chem. Soc. 1998, 120, 9417, or Tetrahedron Lett. 1998, 39, 3899, there was a problem in that steric control of a phosphorus atom is not possible.

A method of synthesizing a boranophosphate oligomer described in T. Angew. Chem. Int. Ed. 2009, 48, 496-499 or RSC Adv. 2015, 5, 2392-2395 is useful in that steric control of a phosphorus atom is possible; however, there was a problem in that a side reaction occurred in a base moiety protected by a protecting group upon boronation of a phosphorus atom.

By the above-described side reaction, synthesis of a boranophosphate oligomer containing a nucleoside having only a thymine (T) structure or a uracil (U) structure as a base is possible, but it was difficult to synthesize a boranophosphate oligomer containing a nucleoside having a base having an amino group (—$NH2$) such as an adenine (A) structure, a cytosine (C) structure, or a guanine (G) structure.

In a method of synthesizing a boranophosphate oligomer described in Tetrahedron Lett. 2012, 53, 4361-4364, a protecting group of a base moiety is removed together with an asymmetric auxiliary group of a phosphorus atom, under acidic conditions.

Thus, since no side reaction of a base moiety occurs upon boronation described above, it is possible to stereoselectively synthesize a boranophosphate oligomer containing a nucleoside having a base having an amino group such as an adenine structure, cytosine structure, or guanine structure, as well as a thymine structure or uracil structure.

In the present disclosure, stereoselectively synthesizing a boranophosphate oligomer refers to performing synthesis under controlling whether any one of two stereoisomers (Rp isomer or Sp isomer) having the phosphorus atom as an asymmetric center is included for each monomer unit (a nucleotide unit in which one of the non-bridging oxygen atoms of a phosphodiester structure is substituted with a borano group (—$BH_3$)).

In the method of synthesizing a boranophosphate oligomer according to Tetrahedron Lett. 2012, 53, 4361-4364, the asymmetric auxiliary group has a tertiary carbon atom and a steric hindrance by the asymmetric auxiliary group is large, in order to enable deprotection under acidic conditions.

Thus, there was a problem in that reactivity of a polymerizable compound is low and stereoselectivity of a condensation reaction is reduced, for example, about 1 to 2%.

Due to the above-mentioned problems, according to a method of synthesizing a boranophosphate oligomer related to Tetrahedron Lett. 2012, 53, 4361-4364, for example, it was difficult to synthesize a long chain oligomer such as a decamer or higher oligomer.

As a result of intensive studies, the present inventors found that the polymerizable compound according to the present disclosure is highly reactive and allows stereoselective synthesis of an oligomer (for example, a boranophosphate oligomer), regardless of whether a base in a nucleoside has an amino group.

The monomer according to the present disclosure has no tertiary carbon atom described above, is highly reactive due to small steric hindrance, and allows synthesis of a long chain oligomer of, for example, a decamer or higher oligomer. Also, since a protecting group of a base moiety is removed together with an asymmetric auxiliary group of a phosphorus atom, under an acidic condition, for example, in the case of DNA synthesis, the monomer is considered to allow stereoselective synthesis of a boranophosphate oligomer in which each of four base species of A, T, C, and G is freely combined, regardless of whether a base in a nucleoside has an amino group.

In addition, the compound according to the present disclosure is a novel compound which is an intermediate of synthesis of the boranophosphate oligomer.

In addition, according to the method of producing a boranophosphate oligomer according to the present disclosure, it has been found that it is possible to synthesize a long chain oligomer of, for example, a decamer or higher oligomer, and also, it is possible to stereoselectively synthesize a boranophosphate oligomer in which a polymerizable compound containing a nucleoside in which a base has an amino group and a polymerizable compound containing a nucleoside in which a base has no amino group are freely combined.

An object of the present invention is to provide a polymerizable compound which is highly reactive and allows stereoselective synthesis of a boranophosphate oligomer, regardless of whether a base in a nucleoside has an amino group.

In addition, another object of the present invention is to provide a novel compound.

Further, another object of the present invention is to provide a method of producing a boranophosphate oligomer, which has high yield and stereoselectivity, and allows stereoselective synthesis of a boranophosphate oligomer, regardless of whether a base in a nucleoside has an amino group.

As means for solving the above problems, the following embodiments are included.

<1>

A polymerizable compound represented by the following Formula A-1 or Formula A-2.

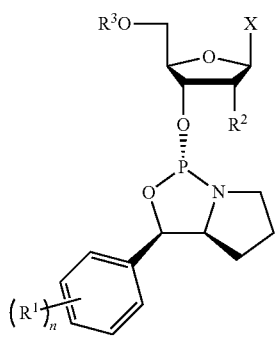

A-1

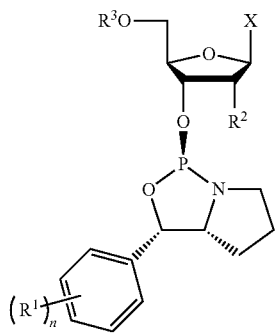

A-2

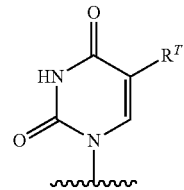

B-1

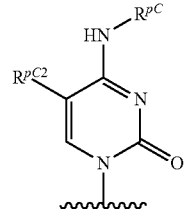

B-2

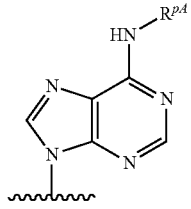

B-3

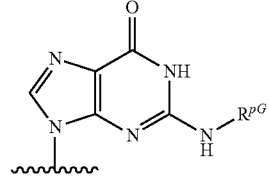

B-4

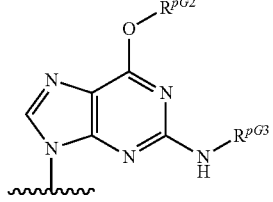

B-5

In Formula A-1 or Formula A-2, $R^1$ represents an electron-donating group; n represents an integer from 1 to 5; $R^2$ represents a hydrogen atom, a halogen atom, or —$OR^O$, wherein $R^O$ represents a hydrogen atom, an alkyl group, or a protecting group of a hydroxy group; $R^3$ represents a hydrogen atom or a protecting group of a hydroxy group; and X represents a structure represented by any one of Formula B-1 to Formula B-5.

In Formula B-1 to Formula B-5, $R^T$ represents a hydrogen atom, an alkyl group, an alkenyl group, or an alkynyl group; each of $R^{pC}$, $R^{pA}$, and $R^{pG}$ represents a protecting group that is removed under an acidic condition; $R^{pC2}$ represents a hydrogen atom or an alkyl group; $R^{pG2}$ represents a protecting group; $R^{pG3}$ represents a protecting group that is removed under an acidic condition, or a hydrogen atom; and a wavy line ($\sim$) represents a binding site to another structure.

<2>

A compound including a structural unit represented by the following Formula T-1 and a structural unit represented by the following Formula D-1 or Formula D-2.

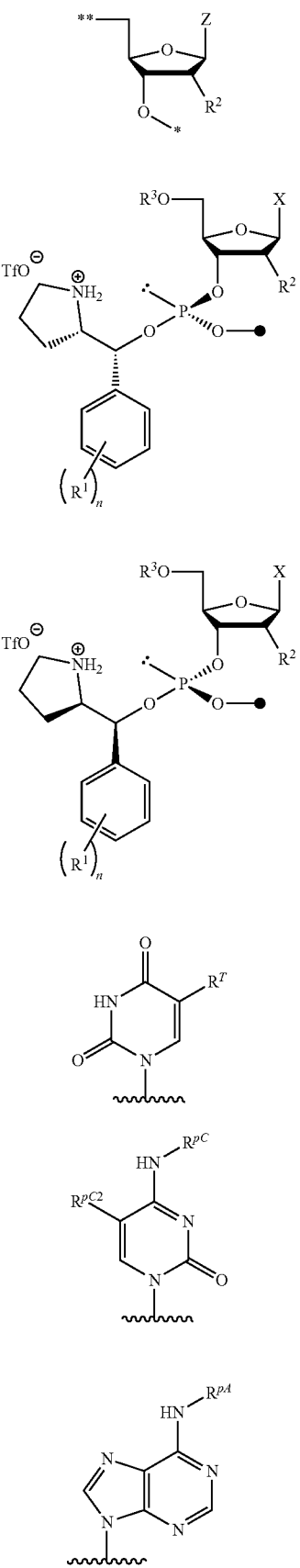
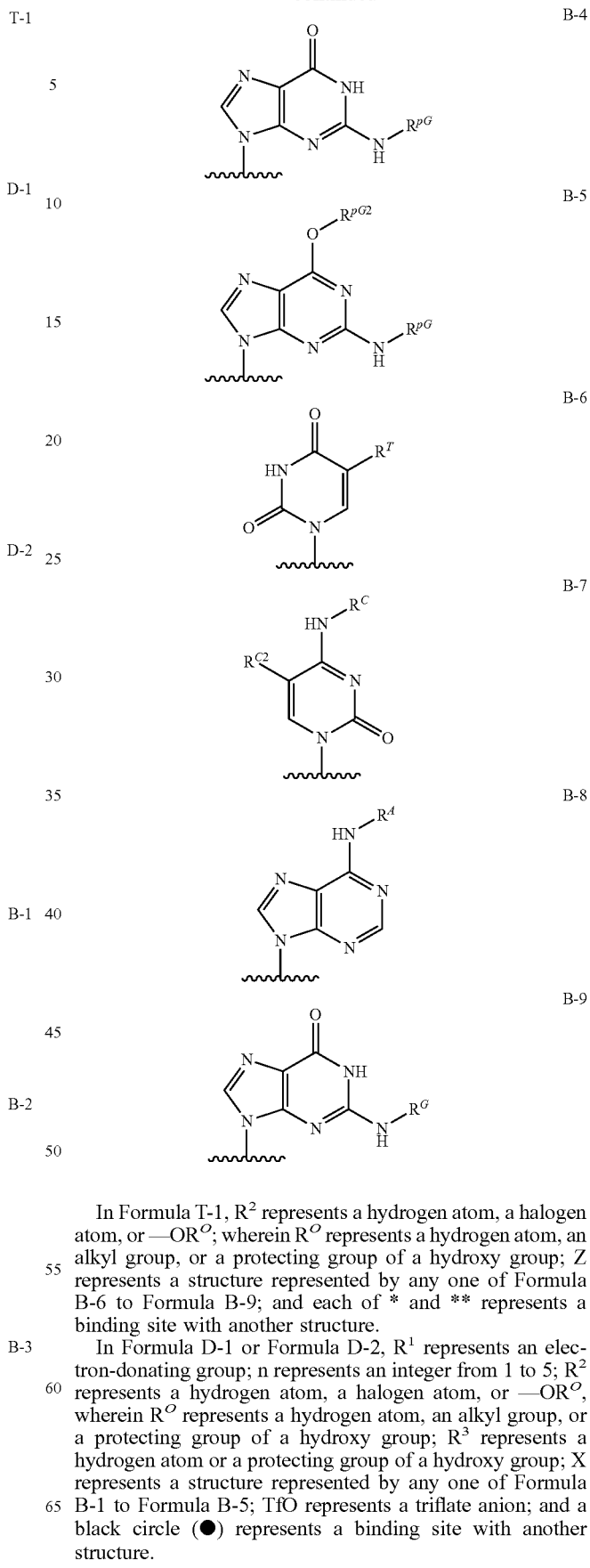

In Formula T-1, R² represents a hydrogen atom, a halogen atom, or —OR^O; wherein R^O represents a hydrogen atom, an alkyl group, or a protecting group of a hydroxy group; Z represents a structure represented by any one of Formula B-6 to Formula B-9; and each of * and ** represents a binding site with another structure.

In Formula D-1 or Formula D-2, $R^1$ represents an electron-donating group; n represents an integer from 1 to 5; $R^2$ represents a hydrogen atom, a halogen atom, or —OR^O, wherein R^O represents a hydrogen atom, an alkyl group, or a protecting group of a hydroxy group; $R^3$ represents a hydrogen atom or a protecting group of a hydroxy group; X represents a structure represented by any one of Formula B-1 to Formula B-5; TfO represents a triflate anion; and a black circle (●) represents a binding site with another structure.

In Formula B-1 to Formula B-5, $R^T$ represents a hydrogen atom, an alkyl group, an alkenyl group, or an alkynyl group; each of $R^{pC}$, $R^{pA}$, and $R^{pG}$ represents a protecting group that is removed under an acidic condition; $R^{pC2}$ represents an alkyl group; $R^{pG2}$ represents a protecting group; $R^{pG3}$ represents a protecting group that is removed under an acidic condition or a hydrogen atom; and a wavy line ( ⁓ ) represents a binding site to another structure.

In Formula B-6 to Formula B-9, $R^T$ represents a hydrogen atom, an alkyl group, an alkenyl group, or an alkynyl group; $R^C$, $R^A$, and $R^G$ represent a hydrogen atom; and a wavy line ( ⁓ ) represents a binding site to another structure.

<3>

A compound described in <2>, further including one or both structural units represented by the following Formula C-1 or Formula C-2.

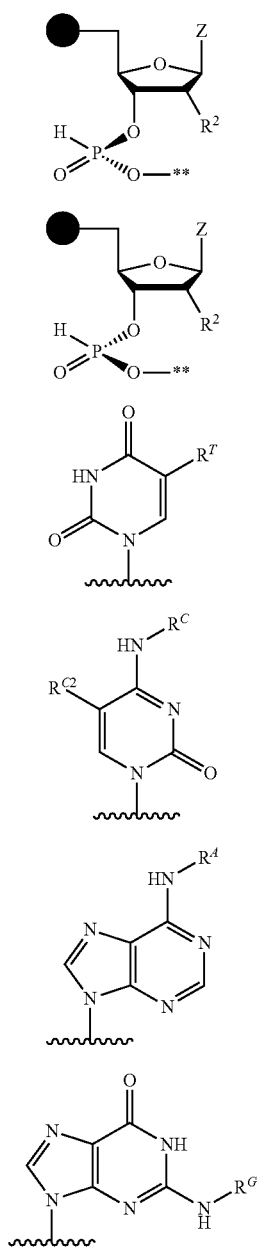

In Formula C-1 or Formula C-2, $R^2$ represents a hydrogen atom, a halogen atom, or $-OR^O$; $R^O$ represents a hydrogen atom, an alkyl group, or a protecting group of a hydroxy group; Z represents a structure represented by any one of Formula B-6 to Formula B-9; and each of ** and a black circle (●) represents a binding site with another structure.

In Formula B-6 to Formula B-9, $R^T$ represents a hydrogen atom, an alkyl group, an alkenyl group, or an alkynyl group; each of $R^C$, $R^A$, and $R^G$ represents a hydrogen atom; and a wavy line ( ⁓ ) represents a binding site to another structure.

<4>

A method of producing a boranophosphate oligomer, including a step of condensing the polymerizable compound described in <1>.

According to an embodiment of the present invention, there can be provided a polymerizable compound which is highly reactive and allows stereoselective synthesis of a boranophosphate oligomer, regardless of whether a base in a nucleoside has an amino group.

In addition, according to another embodiment of the present invention, a novel compound is provided.

Further, according to another embodiment of the present invention, there can be provided a method of producing a boranophosphate oligomer, which has high stereoselectivity and yield, and allows stereoselective synthesis of a boranophosphate oligomer, regardless of whether a base in a nucleoside has an amino group.

DESCRIPTION OF EMBODIMENTS

Figure 1:
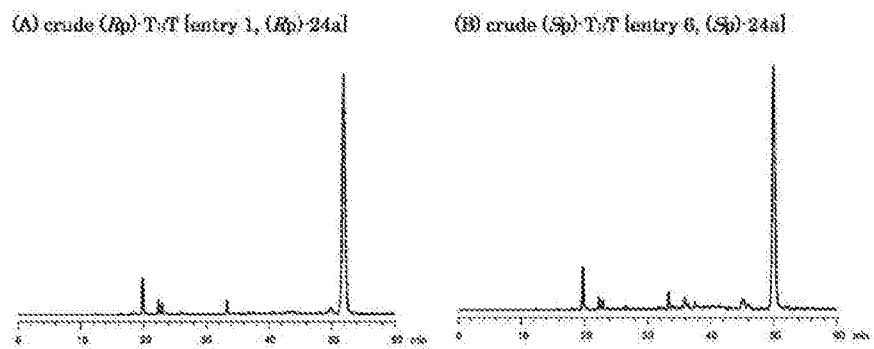
FIG. 1 shows HPLC charts showing results of reverse phase HPLC of (A) a synthesis reaction solution (crude) of (Rp)-$T_BT$ [(Rp)-24a] and (B) a synthesis reaction solution (crude) of (Sp)-$T_BT$ [(Sp)-24a].

Hereinafter, the present disclosure will be described in detail.

In addition, the description "xx to yy" herein represents a numerical value including xx and yy.

In addition, in the present disclosure, "% by mass" and "% by weight" are synonymous and "parts by mass" and "part by weight" are synonymous.

In addition, in the present disclosure, a combination of two or more preferred embodiments is a more preferred embodiment.

In the present disclosure, regarding a representation of a group in a compound represented by a formula, when "substituted or unsubstituted" is not described and the group can further have a substituent, not only an unsubstituted group but also a substituted group is included, unless otherwise specified. For example, in the formula, when it is described that "R represents an alkyl group", it means that "R represents an unsubstituted alkyl group or a substituted alkyl group".

The word "step" herein is included in the term, not only in the case where the step is an independent step, but also even in the case where the step cannot be clearly distinguished from other steps, when an intended purpose of the step is achieved.

Hereinafter, the present disclosure will be described in detail.

(Polymerizable Compound)

The polymerizable compound according to the present disclosure is a compound represented by the following Formula A-1 or Formula A-2.

It is preferred that the polymerizable compound according to the present disclosure is a polymerizable compound for forming a boranophosphate oligomer.

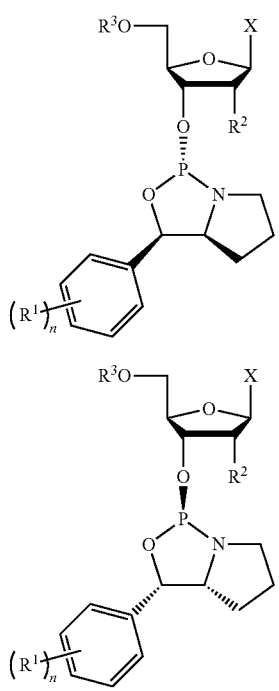

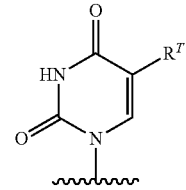

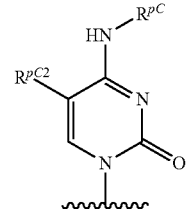

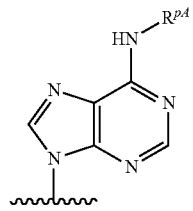

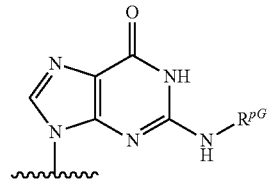

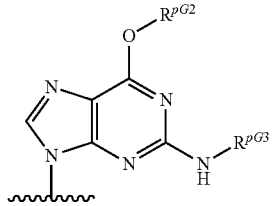

In Formula A-1 or Formula A-2, $R^1$ represents an electron-donating group; n represents an integer of 1 to 5; $R^2$ represents a hydrogen atom, a halogen atom, or —$OR^O$; $R^O$ represents a hydrogen atom, an alkyl group, or a protecting group of a hydroxy group; $R^3$ represents a hydrogen atom or a protecting group of a hydroxy group; and X represents a structure represented by any one of Formula B-1 to Formula B-5.

In Formula B-1 to Formula B-5, $R^T$ represents a hydrogen atom, an alkyl group, an alkenyl group, or an alkynyl group; each of $R^{pC}$, $R^{pA}$, and $R^{pG}$ represents a protecting group that is removed under acidic conditions; $R^{pC2}$ represents an alkyl group; $R^{pG2}$ represents a protecting group; $R^{pG3}$ represents a protecting group that is removed under an acidic condition or a hydrogen atom; and a wavy line ( ~~~ ) represents a binding site to another structure.

In Formula A-1 or Formula A-2, $R^1$ represents an electron-donating group, and preferably an alkoxy group, —$NR^N_2$, a hydroxy group, an aryl group, or an alkyl group, more preferably an alkoxy group, still more preferably an alkoxy group having 1 to 4 carbon atoms, and particularly preferably a methoxy group.

$R^N$ each independently represents a hydrogen atom or an alkyl group having 1 to 10 carbon atoms.

In Formula A-1 or Formula A-2, n represents an integer of 1 to 5, preferably an integer of 1 to 3, and more preferably 1.

When n is 2 or more, a plurality of $R^1$ may be identical or different from each other.

In Formula A-1 or Formula A-2, $R^2$ represents a hydrogen atom, a halogen atom, or $-OR^O$.

Examples of the halogen atom of $R^2$ include a fluorine atom, a chlorine atom, a bromine atom, and an iodine atom, and a fluorine atom is preferred.

$R^O$ represents a hydrogen atom, an alkyl group, or a protecting group of a hydroxy group, and as a protecting group of a hydroxy group, for example, it is possible to use a protecting group conventionally known as a protecting group used for protecting the hydroxy group at 2-position of a ribose structure commonly used in the synthesis of RNA or its derivative, reference can be also made to protecting groups described in publications such as Green, et al., Protective Groups in Organic Synthesis, 3rd Edition, 1999, John Wiley & Sons, Inc., and examples thereof include an acetyl group, a phenoxyacetyl group, a pivaloyl group, a benzyl group, a 4-methoxybenzyl group, a benzoyl group, a triphenylmethyl group, a 4,4'-dimethoxytrityl (DMTr) group, a 4-methoxytrityl (MMTr) group, a 9-phenylxanthenyl group, a trimethylsilyl group, a cyanomethoxymethyl group, a 2-(cyanoethoxy)ethyl group, and a cyanoethoxymethyl group, and preferably a 4,4'-dimethoxytrityl (DMTr) group.

$R^3$ represents a hydrogen atom or a protecting group of a hydroxy group, and as a protecting group of a hydroxy group, reference can be made to protecting groups described in publications such as Green, et al., Protective Groups in Organic Synthesis, 3rd Edition, 1999, John Wiley & Sons, Inc., and examples thereof include an acetyl group, a phenoxyacetyl group, a pivaloyl group, a benzyl group, a 4-methoxybenzyl group, a benzoyl group, a triphenylmethyl group, a 4,4'-dimethoxytrityl (DMTr) group, a 4-methoxytrityl (MMTr) group, a 9-phenylxanthenyl group, a trimethylsilyl group, a cyanomethoxymethyl group, a 2-(cyanoethoxy)ethyl group, and a cyanoethoxymethyl group, and preferably a 4,4'-dimethoxytrityl (DMTr) group.

In Formula A-1 or Formula A-2, X represents a structure represented by any one of Formula B-1 to Formula B-5, Formula B-1 corresponds to a thymine structure or uracil structure, Formula B-2 corresponds to a cytosine structure, Formula B-3 corresponds to an adenine structure, and Formula B-4 and Formula B-5 correspond to a guanine structure, respectively.

In addition, the thymine structure, the uracil structure, the cytosine structure, the adenine structure, and the guanine structure include each structure having a substituent.

In Formula B-1 to Formula B-5, it is preferred that $R^T$ represents a hydrogen atom, an alkyl group, an alkenyl group, or an alkynyl group, and a hydrogen atom, an alkyl group having 1 to 4 carbon atoms, an alkenyl group having 2 to 4 carbon atoms, or an alkynyl group having 2 to 4 carbon atoms is preferred.

Each of $R^{pC}$, $R^{pA}$, and $R^{pG}$ represent a protecting group that is removed under acidic conditions, reference can be made to protecting groups described in publications such as Green, et al., Protective Groups in Organic Synthesis, 3rd Edition, 1999, John Wiley & Sons, Inc., for example, a tert-butoxycarbonyl group, a benzyloxycarbonyl group, a 4,4'-trimethoxytrityl (TMTr) group, a 4,4'-dimethoxytrityl (DMTr) group, a 4-methoxytrityl (MMTr) group, or 4-methoxybenzyloxycarbonyl (MCBz) group is preferred, and from a viewpoint of reducing steric hindrance and improving reactivity of a monomer, 4-methoxybenzyloxycarbonyl (MCBz) group is more preferred.

$R^{pC2}$ represents a hydrogen atom or an alkyl group, preferably an alkyl group having 1 to 4 carbon atoms, and more preferably a methyl group.

$R^{pG2}$ represents a protecting group, and as the protecting group, for example, it is possible to use a known protecting group of a hydroxy group without limitation, reference can be also made to protecting groups described in publications such as Green, et al., Protective Groups in Organic Synthesis, 3rd Edition, 1999, John Wiley & Sons, Inc., and examples thereof include an acetyl group, a phenoxyacetyl group, a pivaloyl group, a benzyl group, a 4-methoxybenzyl group, a benzoyl group, a triphenylmethyl group, a 4,4'-dimethoxytrityl (DMTr) group, a 4-methoxytrityl (MMTr) group, a 9-phenylxanthenyl group, a trimethylsilyl group, a trimethylsilylethyl group, a cyanomethoxymethyl group, a 2-(cyanoethoxy)ethyl group, and a cyanoethoxymethyl group, and preferably a trimethylsilylethyl group.

In addition, as $R^{pG2}$, a protecting group that is removed under an acidic condition is preferred.

$R^{pG3}$ represents a protecting group or a hydrogen atom that is removed under acidic conditions in $R^{pG}$ described above, and examples of the protecting group include the same protecting group as those removed under an acidic condition, and the same applies to a preferred embodiment thereof.

<Method of Producing a Polymerizable Compound>

Hereinafter, an example of the method of producing a polymerizable compound according to the present disclosure will be described. However, the present disclosure is not limited thereto.

The polymerizable compound according to the present disclosure can be synthesized, for example, according to the following Scheme 1.

In the following Scheme 1, $Et_3N$ is triethylamine.

In the following Scheme 1, (Rp)or(Sp)-20a-d is a compound represented by Formula A-1 or Formula A-2.

Scheme 1

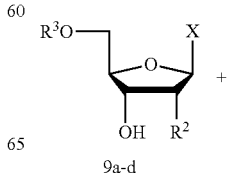

9a-d

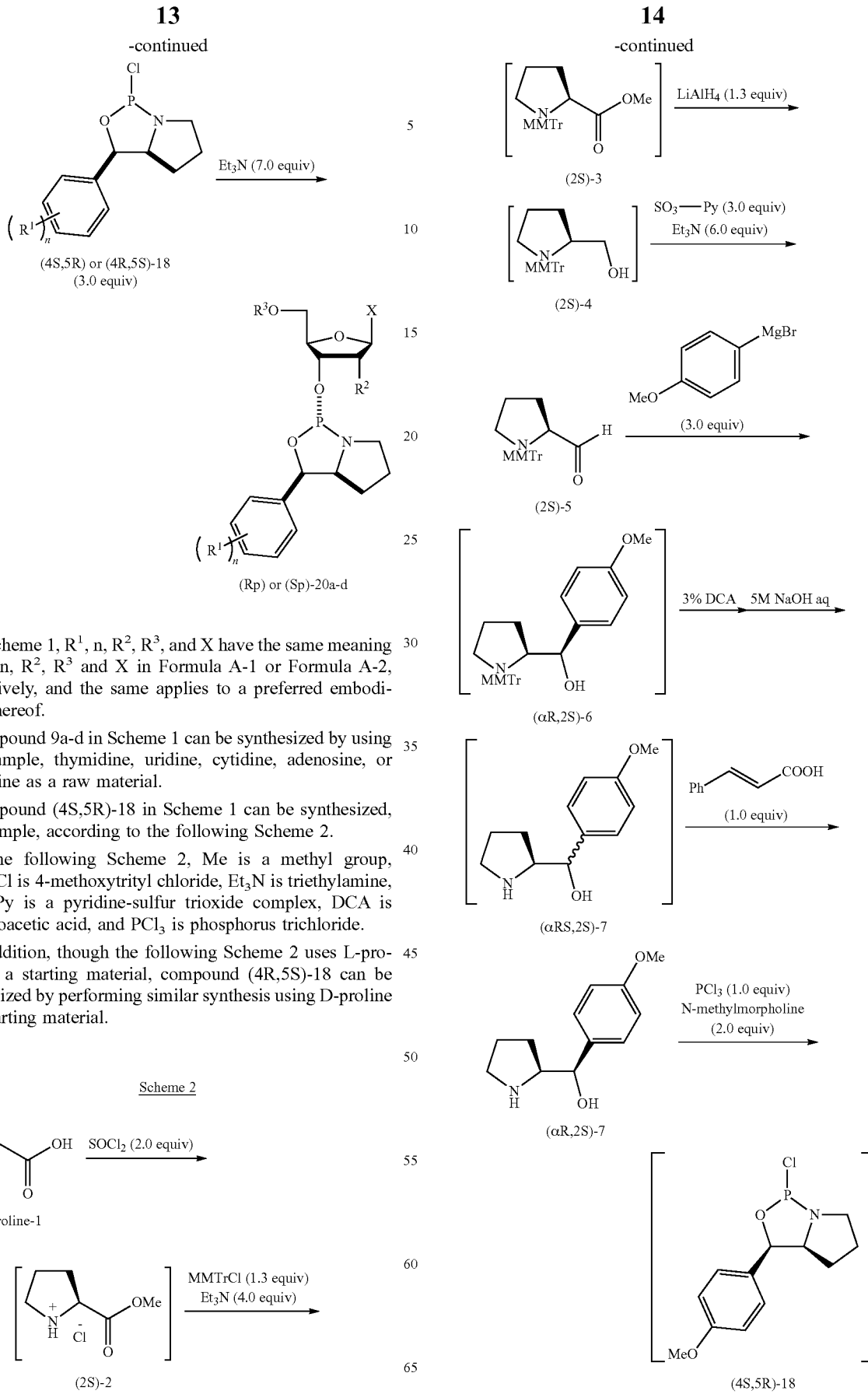

In Scheme 1, $R^1$, n, $R^2$, $R^3$, and X have the same meaning as $R^1$, n, $R^2$, $R^3$ and X in Formula A-1 or Formula A-2, respectively, and the same applies to a preferred embodiment thereof.

Compound 9a-d in Scheme 1 can be synthesized by using, for example, thymidine, uridine, cytidine, adenosine, or guanosine as a raw material.

Compound (4S,5R)-18 in Scheme 1 can be synthesized, for example, according to the following Scheme 2.

In the following Scheme 2, Me is a methyl group, MMTrCl is 4-methoxytrityl chloride, $Et_3N$ is triethylamine, $SO_3$—Py is a pyridine-sulfur trioxide complex, DCA is dichloroacetic acid, and $PCl_3$ is phosphorus trichloride.

In addition, though the following Scheme 2 uses L-proline as a starting material, compound (4R,5S)-18 can be synthesized by performing similar synthesis using D-proline as a starting material.

(Method of Producing Boranophosphate Oligomer)

A method of producing a boranophosphate oligomer according to the present disclosure is a method of producing a boranophosphate oligomer, the method including a step of condensing a polymerizable compound according to the present disclosure (hereinafter, also referred to as "condensation step").

Hereinafter, an example of the method of producing a boranophosphate oligomer according to the present disclosure will be described. However, the present disclosure is not limited thereto.

<Condensation Step>

A condensation step in the present disclosure follows, for example, the following Scheme 3.

Subsequently, an oligomer chain is extended by repeating a condensation reaction and deprotection of an asymmetric auxiliary group, a protecting group of a base, and $R^3$, using the polymerizable compound and an activator. Deprotection of the asymmetric auxiliary group and the protecting group of a base is performed under an acidic condition. By using a protecting group that is removed under acidic conditions as $R^3$, it is possible to perform deprotection of $R^3$ simultaneously with the deprotection of the asymmetric auxiliary group and the protecting group of a base.

In Scheme 3, though the polymerizable compound 20a-d and compound 21 (CMPT, N-(cyanomethyl)pyrrolidinium triflate) which is an activator are used, the activator is not limited thereto and can be changed.

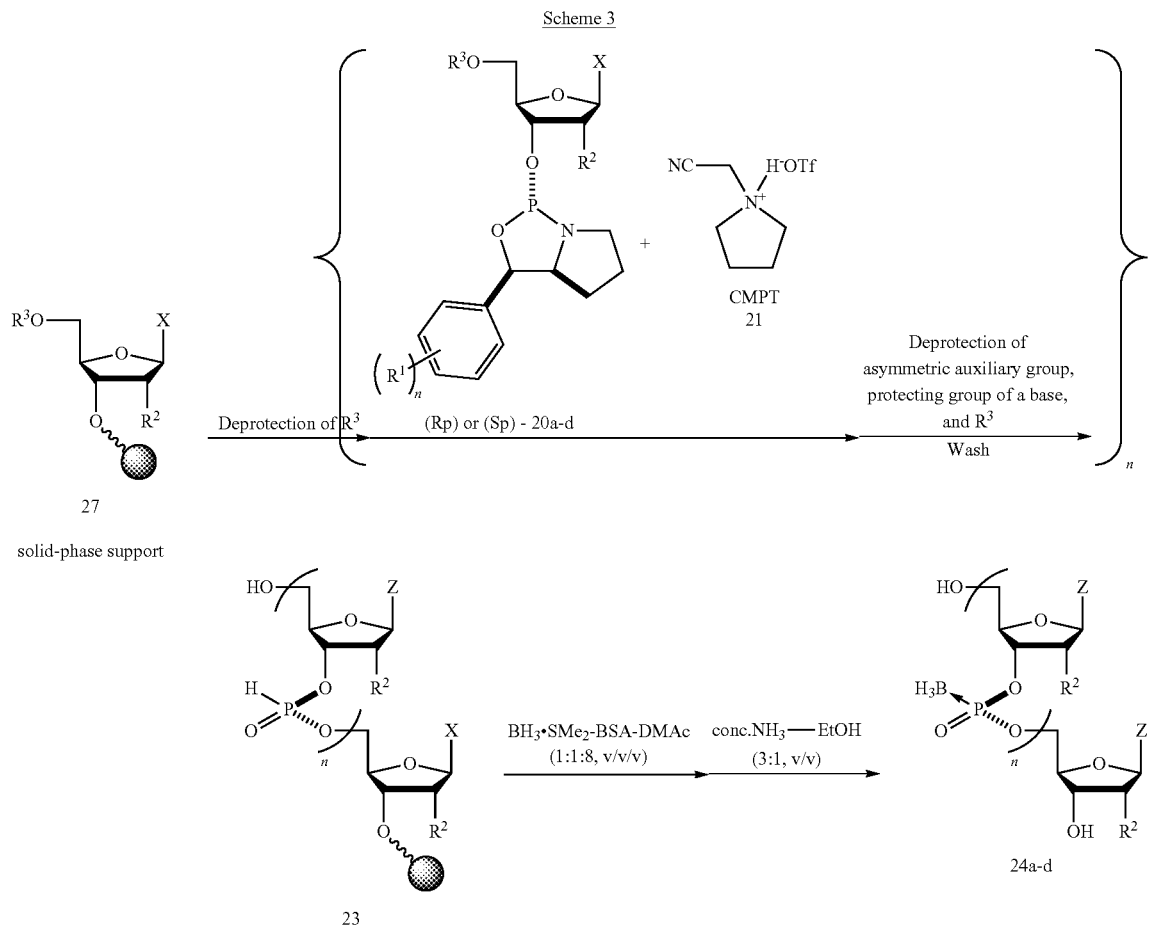

Scheme 3

In Scheme 3, $R^1$, n, $R^2$, $R^3$, and X have the same meaning as $R^1$, n, $R^2$, $R^3$, and X in Formula A-1 or Formula A-2, respectively, and the same applies to a preferred embodiment thereof.

In addition, in Scheme 3, Z represents a structure represented by any one of Formula B-6 to Formula B-9 described later.

In Scheme 3, deprotection of $R^3$ is performed in Compound 27 loaded on a solid support. The deprotection of $R^3$ is performed, for example, under acidic conditions.

After H-phosphonate oligomer 23 is formed, boronation is performed, thereby boranophosphate oligomer 24a-d is obtained.

In Scheme 3, though a synthesis method by a solid phase method is shown, it is possible to perform synthesis by a liquid phase method by the same scheme.

From a viewpoint of stereoselectivity and reaction rate, it is preferred to perform synthesis by a solid phase method.

In Scheme 3, details of an extension reaction of an oligomer chain are shown in the following Scheme 4.

Scheme 4

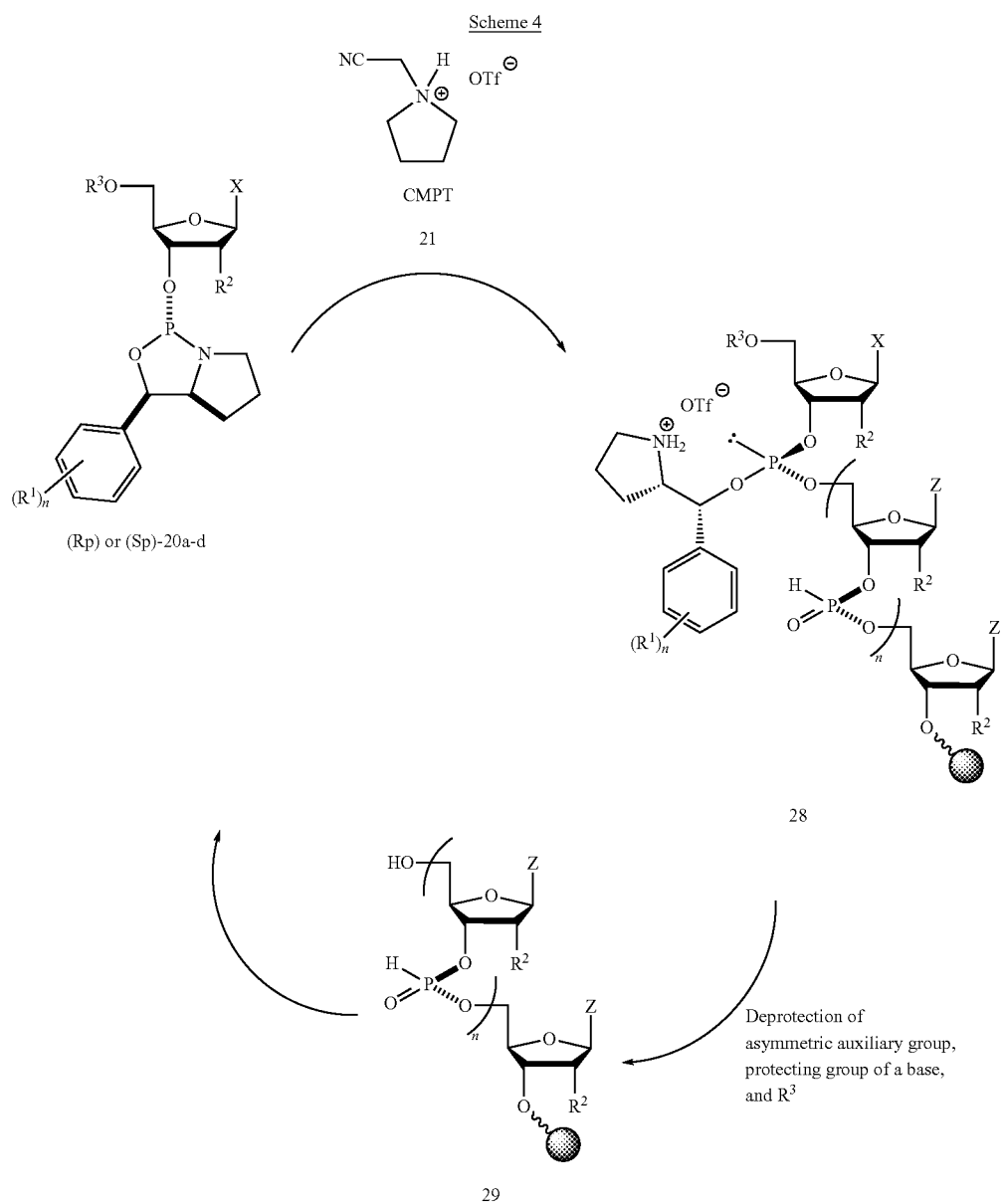

In Scheme 4, $R^1$, n, $R^2$, $R^3$, and X each independently have the same meaning as $R^1$, n, $R^2$, $R^3$, and X in Formula A-1 or Formula A-2, and the same applies to a preferred embodiment thereof.

n represents an integer of 0 to 100, preferably an integer of 1 to 100, more preferably an integer of 9 to 100, and still more preferably an integer of 11 to 100.

In Scheme 4, TfO (OTf) represents a triflate anion, and Z represents a structure represented by any one of Formula B-6 to Formula B-9 described later.

In Scheme 4, (Rp) or (Sp)-20a-d which is the polymerizable compound according to the present disclosure is bonded to a hydroxy group at 5'-position of a sugar structure at the end of H-phosphonate substituted nucleotide in the presence of an activator 21 and forms an intermediate 28. Thereafter, an asymmetric auxiliary group from the intermediate 28, a protecting group of a base, and $R^3$ are deprotected to form an oligomer 29. Further, (Rp) or (Sp)-20a-d is bonded to a hydroxy group at 5'-position of a sugar structure at the end of the oligomer 29. This is repeated to extend the oligomer chain.

In Scheme 4, though for convenience, all configurations in which a phosphorus atom contained in the intermediate 28 or the oligomer 29 is an asymmetric point is described as an S configuration (Sp isomer), a compound represented by Formula A-1 and a compound represented by Formula A-2 are properly used as a monomer, whereby an H-phosphonate structure of a S configuration (Sp isomer) and an H-phosphonate structure of a R configuration (Rp isomer) can be introduced at any position.

That is, the intermediate 28 is a compound including a structural unit represented by the following Formula T-1 and a structural unit represented by the following Formula D-1 or D-2.

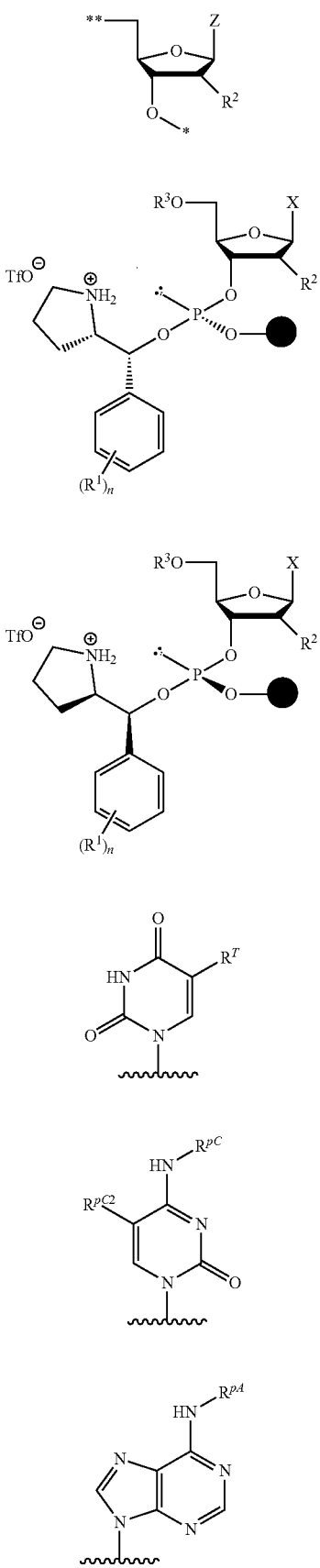
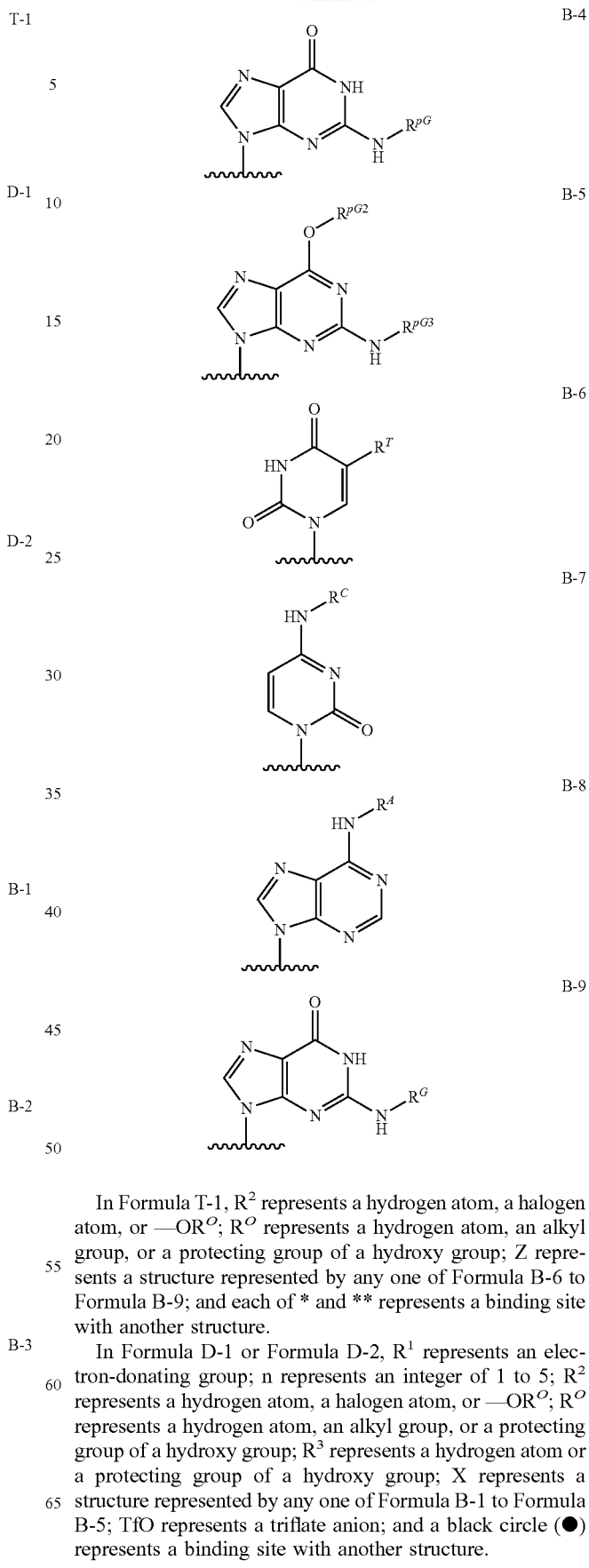

In Formula T-1, $R^2$ represents a hydrogen atom, a halogen atom, or —$OR^O$; $R^O$ represents a hydrogen atom, an alkyl group, or a protecting group of a hydroxy group; Z represents a structure represented by any one of Formula B-6 to Formula B-9; and each of * and ** represents a binding site with another structure.

In Formula D-1 or Formula D-2, $R^1$ represents an electron-donating group; n represents an integer of 1 to 5; $R^2$ represents a hydrogen atom, a halogen atom, or —$OR^O$; $R^O$ represents a hydrogen atom, an alkyl group, or a protecting group of a hydroxy group; $R^3$ represents a hydrogen atom or a protecting group of a hydroxy group; X represents a structure represented by any one of Formula B-1 to Formula B-5; TfO represents a triflate anion; and a black circle (●) represents a binding site with another structure.

In Formula B-1 to Formula B-5, $R^T$ represents a hydrogen atom, an alkyl group, an alkenyl group, or an alkynyl group; each of $R^{pC}$, $R^{pA}$, and $R^{pG}$ represents a protecting group that is removed under acidic conditions; $R^{pC2}$ represents a hydrogen atom or an alkyl group; $R^{pG2}$ represents a protecting group; $R^{pG3}$ represents a protecting group that is removed under an acidic condition or a hydrogen atom; and a wavy line (∿) represents a binding site to another structure.

In Formula B-6 to Formula B-9, $R^T$ represents a hydrogen atom, an alkyl group, an alkenyl group, or an alkynyl group; $R^C$, $R^A$, and $R^G$ represent a hydrogen atom; $R^{C2}$ represents a hydrogen atom or an alkyl group; and a wavy line represents a binding site to another structure.

In Formula T-1, $R^2$ has the same meaning as $R^2$ in Formula A-1 or Formula A-2, and the same applies to a preferred embodiment thereof.

In Formula T-1, * represents a binding site to another structure, and when the synthesis is performed by solid phase synthesis, it is preferred that * represents a binding site to a support.

In Formula T-1, Z is preferably a structure represented by any one of Formula B-6 to Formula B-9, and more preferably any one of a thymine structure, a uracil structure, a cytosine structure, an adenine structure, or a guanine structure.

In Formula D-1 and Formula D-2, $R^1$, n, $R^2$, $R^3$, and X have the same meaning as $R^1$, n, $R^2$, $R^3$, and X in Formula A-1 or Formula A-2, and the same applies to a preferred embodiment thereof.

Formula B-1 to Formula B-5 have the same meaning as Formula B-1 to Formula B-5 in Formula A-1 or Formula A-2 described above, and the same applies to a preferred embodiment thereof.

According to a method of producing a boranophosphate oligomer according to the present disclosure, both boranophosphate DNA and boranophosphate RNA can be produced, depending on the selection of a polymerizable compound used in the condensation step.

In the present disclosure, boranophosphate DNA refers to DNA in which one of non-bridging oxygen atoms in a phosphodiester structure of natural DNA is substituted by a borano group (—$BH_3$).

In the present disclosure, boranophosphate RNA refers to RNA in which one of non-bridging oxygen atoms in a phosphodiester structure of natural RNA is substituted by a borano group (—$BH_3$).

In any one of the DNA and RNA, it is possible to select the polymerizable compound according to the embodiment so that a base sequence is complementary to a base sequence of a target nucleic acid and perform synthesis.

In addition, the compound may further include any one or both of structural units represented by the following Formula C-1 or Formula C-2.

The structural unit represented by the following Formula C-1 or Formula C-2 is a structural unit which is increased by one by one cycle of a condensation cycle described in Scheme 4 described above, and may exist in plural.

The total number of the structural units represented by Formula C-1 or Formula C-2 included in the compound is preferably 9 to 100, and more preferably 11 to 50.

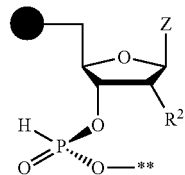
C-1

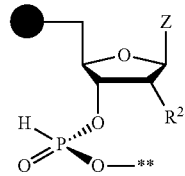
C-2

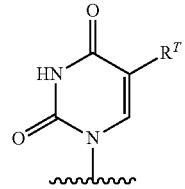
B-6

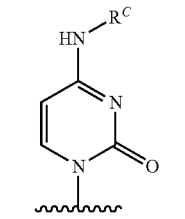
B-7

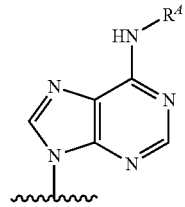
B-8

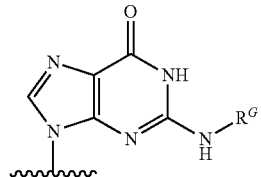
B-9

In Formula C-1 or Formula C-2, $R^2$ represents a hydrogen atom or —$OR^O$; $R^O$ represents a hydrogen atom, an alkyl group, or a protecting group of a hydroxy group; Z represents a structure represented by any one of Formula B-6 to Formula B-9; and ** and a black circle (●) represent a binding site with another structure.

In Formula B-6 to Formula B-9, $R^T$ represents a hydrogen atom, an alkyl group, an alkenyl group, or an alkynyl group; $R^C$, $R^A$, and $R^G$ represent a hydrogen atom; $R^{C2}$ represents a hydrogen atom or an alkyl group; and a wavy line (∿) represents a binding site to another structure.

In Formula C-1 and Formula C-2, Z and $R^2$ have the same meaning as Z and $R^2$ in Formula T-1, respectively, and the same applies to a preferred embodiment thereof.

When a structure represented by Formula C-1 or Formula C-2 exists in plural, a plurality of Z and $R^2$ in Formula C-1 or Formula C-2 may be the same or different.

Formula B-6 to Formula B-9 have the same meaning as Formula B-6 to Formula B-9 in Formula T-1 described above, and the same applies to a preferred embodiment thereof.

In addition, the compound may further include a structural unit derived from at least one selected from the group consisting of the polymerizable compound represented by the following Formula E-1 to Formula E-4.

In the condensation step of the present disclosure, at least one polymerizable compound selected from the group consisting of the polymerizable compound represented by Formula E-1 to Formula E-4 may be further used as other polymerizable compounds.

That is, the boranophosphate oligomer produced by the method of producing a boranophosphate oligomer according to the present disclosure may be boranophosphate LNA.

In the present disclosure, LNA refers to an RNA derivative having a structure in which an oxygen atom at 2'-position and a carbon atom at 4'-position of a ribose ring are crosslinked via methylene, and boranophosphate LNA refers to LNA in which one of non-bridging oxygen atoms in a phosphodiester structure of LNA is substituted by a borano group ($—BH_3$).

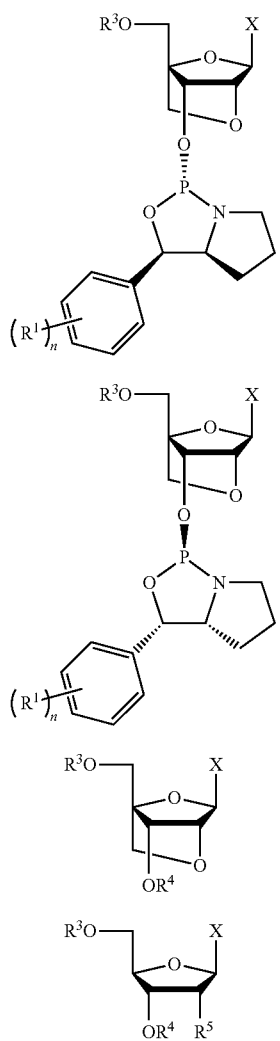

In Formula E-1 to Formula E-4, $R^1$, n, $R^3$, and X have the same meaning as $R^1$, n, $R^3$, and X in Formula A-1 or Formula A-2, and the same applies to a preferred embodiment thereof.

In Formula E-3 and Formula E-4, $R^4$ represents a protecting group of a hydroxy group, and any of those exemplified as the protecting group of a hydroxy group in $R^3$ described above can be used without limitation.

$R^5$ represents a hydrogen atom, a hydroxy group having a protecting group, a halogen atom, or an alkoxy group.

When the polymerizable compound represented by Formula E-1 or Formula E-2 is used in the method of synthesizing of a boranophosphate oligomer according to the present disclosure, it is possible to perform synthesis by the same method as the case where the polymerizable compound represented by Formula A-1 or Formula A-2 is used.

In addition, when a polymerizable compound represented by Formula E-3 or Formula E-4 is used in the method of synthesizing a boranophosphate oligomer according to the present disclosure, it is possible to perform synthesis by a known method of synthesizing DNA or RNA, using a known condensation reagent.

By using the polymerizable compound represented by Formula E-3 or Formula E-4, it is possible to synthesize a boranophosphate oligomer partially including a phosphodiester structure.

<Purification Step>

The method of producing a boranophosphate oligomer according to the present disclosure may further include a step of producing a boranophosphate oligomer (purification step).

In a purification step, the boranophosphate oligomer is purified by a known purification method such as reverse phase high performance liquid chromatography (reverse phase HPLC), ion exchange HPLC, column chromatography, or recrystallization.

In the method of producing a boranophosphate oligomer according to the present disclosure is preferably a method of producing a boranophosphate oligomer of a 10-mer to a 100-mer, more preferably a method of producing a boranophosphate oligomer of a 10-mer to a 50-mer, and still more preferably a method of producing a boranophosphate oligomer of a 12-mer to a 50-mer.

According to the method of producing a boranophosphate oligomer according to the present disclosure, it is possible to produce a boranophosphate oligomer in which the Sp isomer and the Rp isomer described above are freely combined.

For example, by forming only both ends of the boranophosphate oligomer as an Rp isomer and the other structure as a Sp isomer, it is possible to produce a boranophosphate oligomer having improved enzyme resistance.

The boranophosphate oligomer obtained by the method of producing a boranophosphate oligomer according to the present disclosure can be used as an antisense molecule having excellent duplex formation ability to a target nucleic acid, by designing the boranophosphate oligomer to be complementary to a base sequence of a target nucleic acid.

For example, when the target nucleic acid corresponds to a partial sequence of a disease-associated gene, the boranophosphate oligomer is preferably used in a medical use such as an antisense drug having high translation inhibition ability.

Furthermore, application to boron neutron capture therapy (BNCT) can be also considered.

EXAMPLES

Hereinafter, the present disclosure will be described in detail by way of the Examples, but the present disclosure is not limited thereto.

In addition, in the following description, "%" is based on mass, unless otherwise specified.

Details of analysis equipment used in the Examples are as follows.

$^1$H-nuclear magnetic resonance spectrum ($^1$H-NMR): JNM-LA 400 (400 MHz)

$^{31}$P-nuclear magnetic resonance spectrum ($^{31}$P-NMR): JNM-LA 400 (161.8 MHz)

In addition, in $^1$H-NMR, tetramethylsilane (TMS) is used as an internal standard, and in $^{31}$P-NMR, 85% $H_3PO_4$ is used as an external standard.

ESI-MS: Varian 910-MS

Details of terms used in the Examples are as follows.
MMTr=4-methoxytrityl
DMTr=4,4'-dimethoxytrityl
TBS=tert-butyldimethylsilyl
TMS=trimethylsilyl
TFA=trifluoroacetic acid
DCA=dichloroacetic acid
MCbz=4-methoxybenzyloxycarbonyl
Tse=trimethylsilylethyl
CDI=1,1'-carbonyldiimidazole
HMDS=hexamethyldisilazane
DEAD=diethylazodicarboxylate
CMPT=N-(cyanomethyl)pyrrolidinium tri fluoromethanesulfonate
DMAc=N,N-dimethylacetamide
BSA=N,O-bis(trimethylsilyl)acetamide
Th (T)=thymine
Cy (C)=cytosine
Ad (A)=adenine
Gu (G)=guanine

EXAMPLES AND COMPARATIVE EXAMPLES

<Synthesis of Polymerizable Compound>

[Synthesis of (2S)-5]L-proline (1) (11.51 g, 100 mmol) was dissolved in MeOH (100 mL) and cooled to 0° C. To the solution, $SOCl_2$ (14.42 mL, 200 mmol) was slowly added with a dropping funnel. The reaction mixture was stirred at room temperature for 3 hours, and the solvent was removed under reduced pressure to obtain (2S)-2 as a crude product. (2S)-2 was used for the next step, without further purification.

The crude product (2S)-2 was repeatedly azeotropically dried with toluene and $CHCl_3$, and dissolved in $CH_2Cl_2$ (250 mL), and $Et_3N$ (55.75 mL, 400 mmol) and MMTrCl (40.14 g, 130 mmol) were added thereto. The reaction mixture was stirred at room temperature for 17 hours, and a saturated aqueous $NH_4Cl$ solution-concentrated aqueous $NH_3$ solution (2:1, v/v) (150 mL) was added thereto. The organic layer was separated and washed with a saturated aqueous $NaHCO_3$ solution (3×100 mL), and the collected washing liquid was extracted with $CH_2Cl_2$ (100 mL). The collected organic layer was dried over anhydrous $Na_2SO_4$, filtered, and concentrated under reduced pressure to obtain (2S)-3 as a crude product. (2S)-3 was used for the next step, without further purification.

The crude product (2S)-3 was repeatedly azeotropically dried with pyridine, toluene, and $CHCl_3$, then dissolved in THF (100 mL). The solution was slowly added to a THF solution (100 mL) of $LiAlH_4$ (4.93 g, 130 mmol) at 0° C. with a dropping funnel. The reaction mixture was stirred at room temperature for 12 hours, and cooled to 0° C., and $H_2O$ (5 mL), a 15% aqueous NaOH solution (5 mL), and $H_2O$ (15 mL) were sequentially slowly added with a dropping funnel. The reaction mixture was stirred at room temperature for 30 minutes, anhydrous $MgSO_4$ was added thereto, and the mixture was stirred for another 30 minutes. The suspension was filtered through Celite and washed with AcOEt (500 mL). The solution was concentrated under reduced pressure and to the residue $CH_2Cl_2$ (300 ml) was added. Washing was performed with a saturated aqueous $NaHCO_3$ solution (3×100 mL), and the collected washing liquid was extracted with $CH_2Cl_2$ (100 mL). The collected organic layer was dried over anhydrous $Na_2SO_4$, filtered, and concentrated under reduced pressure to give (2S)-4 as a crude product. (2S)-4 was used for the next step, without further purification.

The crude product (2S)-4 was dissolved in $CH_2Cl_2$ (400 mL), and $Et_3N$ (83.18 mL, 600 mmol) was added thereto. To the solution, a DMSO solution (100 mL) of a pyridine-sulfur trioxide complex (47.75 g, 300 mmol) was added at 0° C. The reaction mixture was stirred at room temperature for 3 hours, and a saturated aqueous $NaHCO_3$ solution (100 mL) was added thereto. The organic layer was separated and washed with saturated aqueous $NaHCO_3$ solutions (3×100 mL), and the collected washing liquid was extracted with $CH_2Cl_2$ (100 mL). The collected organic layer was concentrated under reduced pressure, $Et_2O$ (300 mL) was added to the residue, and washing was performed with a saturated aqueous NaCl solution (5×100 mL). The collected organic layer was dried over anhydrous $Na_2SO_4$, filtered, and concentrated under reduced pressure. The residue was separated and purified by silica gel column chromatography [neutral silica gel, hexane-AcOEt (6:1, v/v), pyridine 1%] to recover a fraction containing (2S)-5. The solvent was removed under reduced pressure to give (2S)-5 as a light yellow foamed material.

$^1$H NMR (400 MHz, $CDCl_3$) δ9.84 (s, 1H), 7.55-7.43 (m, 6H), 7.28-7.14 (m, 6H), 6.82-6.78 (m, 2H), 3.78 (s, 3H), 3.29-3.23 (m, 1H), 2.93-2.87 (m, 1H), 1.64-1.55 (m, 2H), 1.47-1.37 (m, 1H), 1.19-1.10 (m, 1H), 0.90-0.77 (m, 1H). FAB-HRMS: Calcd. for [M+Na]$^+$; 394.1783. Found; 394.1788.

Synthesis of (2R)-5

(2R)-5 was synthesized in the same manner as (2S)-5, using D-proline (1) as a starting material.

$^1$H NMR (300 MHz, $CDCl_3$) δ9.83 (s, 1H), 7.56-7.43 (m, 6H), 7.28-7.12 (m, 6H), 6.84-6.78 (m, 2H), 3.77 (s, 3H), 3.30-3.21 (m, 1H), 2.94-2.85 (m, 1H), 1.65-1.55 (m, 2H), 1.49-1.37 (m, 1H), 1.20-1.08 (m, 1H), 0.90-0.75 (m, 1H). FAB-HRMS: Calcd. for [M+Na]$^+$; 394.1783. Found; 394.1784.

Synthesis of (αR,2S)-7

(2S)-5 (26.00 g, 70 mmol) was repeatedly azeotropically dried with pyridine, toluene, and $CHCl_3$, then dissolved in $Et_2O$ (300 mL) and cooled to −78° C. To the solution, a 0.5 M 4-methoxyphenyl magnesium bromide/THF solution (420 mL, 210 mmol) was slowly added with a dropping funnel. The reaction mixture was stirred at room temperature for 18 hours, and a saturated aqueous $NH_4Cl$ solution-concentrated aqueous $NH_3$ solution (2:1, v/v) (300 mL) was added thereto at 0° C. The suspension was filtered through Celite and washed with $Et_2O$ (300 mL). The organic layer was separated and washed with saturated aqueous $NaHCO_3$ solutions (3×100 mL), and the collected washing liquid was extracted with $Et_2O$ (100 mL). The collected organic layer was dried over anhydrous $Na_2SO_4$, filtered, and concentrated under reduced pressure to give (αR,2S)-6 as a crude product. (αR,2S)-6 was used for the next step, without further purification.

To the crude product (αR,2S)-6, a 3% DCA/CH$_2$Cl$_2$ solution (300 mL) was added. The reaction mixture was stirred at room temperature for 10 minutes, H$_2$O (300 mL) was added thereto, the aqueous layer was separated, washed with CH$_2$Cl$_2$ (5×100 mL), and the collected washing liquid was extracted with water (100 mL). To the collected aqueous layer, a 5 M aqueous NaOH solution was added until the pH reached 11. CH$_2$Cl$_2$ (300 mL) was added thereto, the organic layer was separated and washed with a saturated aqueous NaHCO$_3$ solution (3×100 mL), and the collected washing liquid was extracted with CH$_2$Cl$_2$ (100 mL). The collected organic layer was dried over anhydrous Na$_2$SO$_4$, filtered, and concentrated under reduced pressure to give (αRS,2S)-7.

To (αRS,2S)-7 (5.18 g, 25 mmol), trans-cinnamic acid (3.70 g, 25 mmol) was added and recrystallization was performed using EtOH. To the precipitated crystal, a 2M aqueous KOH solution (100 mL) and CH$_2$Cl$_2$ (100 mL) was added, and the organic layer was separated. Washing was performed with saturated aqueous NaHCO$_3$ solutions (3×100 mL), and the collected washing liquid was extracted with CH$_2$Cl$_2$ (100 mL). The collected organic layer was dried over anhydrous Na$_2$SO$_4$, filtered, and concentrated under reduced pressure to give (αR,2S)-7 as a light yellow oily material.

$^1$H NMR (400 MHz, CDCl$_3$) δ7.30-7.27 (m, 2H), 6.89-6.86 (m, 2H), 4.68 (d, J=4.0 Hz, 1H), 3.80 (s, 3H), 3.42-3.37 (m, 1H), 3.05-2.99 (m, 1H), 2.96-2.91 (m, 1H), 2.43 (br, 2H), 1.79-1.62 (m, 3H), 1.55-1.47 (m, 1H). FAB-HRMS: Calcd. for [M+H]$^+$; 208.1338. Found; 208.1337.

Synthesis of (αS,2R)-7

(αS,2R)-7 was synthesized in the same manner as (αR,2S)-7, using (2R)-5 as a starting material.

$^1$H NMR (400 MHz, CDCl$_3$) δ7.30-7.27 (m, 2H), 6.89-6.86 (m, 2H), 4.66 (d, J=4.0 Hz, 1H), 3.80 (s, 3H), 3.40-3.35 (m, 1H), 3.03-2.98 (m, 1H), 2.94-2.88 (m, 1H), 2.54 (br, 2H), 1.79-1.61 (m, 3H), 1.55-1.46 (m, 1H). FAB-HRMS: Calcd. for [M+H]$^+$; 208.1338. Found; 208.1338.

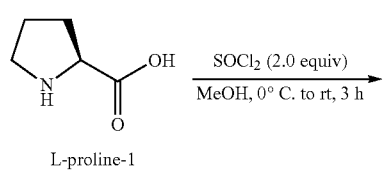

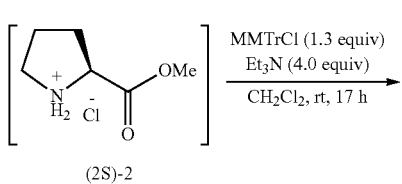

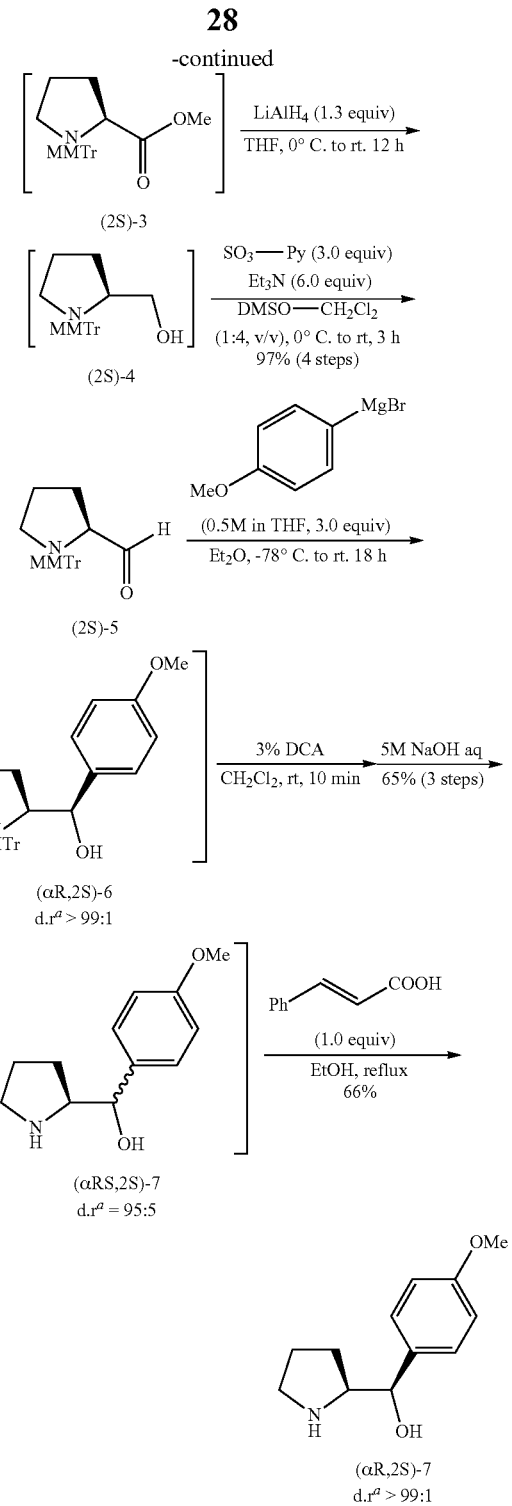

$^a$Determined by $^1$H NMR.

Synthesis of 5′-O-(DMTr)thymidine [9a]

Synthesis was performed according to the method described in the literature, using thymidine (8) as a starting material. $^1$H NMR spectrum was consistent with the literature value.

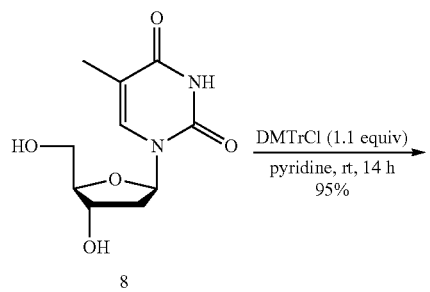

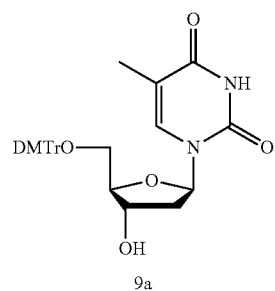

Synthesis of 3',5'-O-bis(TBS)-2'-deoxycytidine [14]

Synthesis was performed according to the method described in the literature, using 2'-deoxycytidine (13) as a starting material. $^1$H NMR spectrum was consistent with the literature value.

Synthesis of 3',5'-O-bis(TBS)-N$^4$-MCbz-2'-deoxycytidine [15]

3',5'-O-bis(TBS)-2'-deoxycytidine (14) (4.55 g, 10 mmol) was repeatedly azeotropically dried with pyridine, toluene, and CHCl$_3$, then dissolved in 1,2-dichloroethane (100 mL), CDI (2.60 g, 16 mmol) was added, and heated to reflux for 20 hours. 4-methoxybenzylalcohol (2.00 mL, 16 mmol) was added thereto, and the mixture was heated to reflux for further 18 hours. A saturated aqueous NaHCO$_3$ solution (100 mL) was added thereto, and the organic layer was separated. Washing was performed with saturated aqueous NaHCO$_3$ solutions (3×100 mL), and the collected washing liquid was extracted with CH$_2$Cl$_2$ (100 mL). The collected organic layer was dried over anhydrous Na$_2$SO$_4$, filtered, and concentrated under reduced pressure. The residue was separated and purified by silica gel column chromatography [neutral silica gel, hexane-AcOEt (1:1, v/v)] to recover a fraction containing 15. The solvent was removed under reduced pressure to give 15 (4.64 g, 7.49 mmol, 75%) as a colorless foamed material.

$^1$H NMR (300 MHz, CDCl$_3$) δ8.38 (d, 1H), 7.46 (br, 1H), 7.34 (d, 2H), 7.18 (d, 1H), 6.93 (d, 2H), 6.25 (t, 1H), 5.15 (s, 2H), 4.41 (q, 1H), 3.98-3.94 (m, 2H), 3.82-3.76 (m, 4H), 2.56-2.47 (m, 1H), 2.17-2.08 (m, 1H), 0.93-0.88 (m, 18H), 0.12-0.05 (m, 12H). FAB-HRMS: Calcd. for [M+H]$^+$; 620.3187. Found; 620.3187.

Synthesis of N$^4$-MCbz-5'-O-DMTr-2'-deoxycytidine [9b]

3',5'-O-bis(TBS)-N$^4$-MCbz-2'-deoxycytidine (15) (4.34 g, 7 mmol) was dissolved in THF (35 mL), 1 M TBAF/THF (35 mL) was added thereto, and stirring was performed at room temperature for 1 hour. A saturated aqueous NaHCO$_3$ solution (100 mL) and AcOEt (300 mL) were added, and the organic layer was separated. Washing was performed with saturated aqueous NaHCO$_3$ solutions (3×100 mL), and the collected washing liquid was extracted with AcOEt (100 mL). The collected organic layer was dried over anhydrous Na$_2$SO$_4$, filtered, and concentrated under reduced pressure. To the residue, pyridine (70 mL) and DMTrCl (2.37 g, 7 mmol) were added, and stirred at room temperature for 14 hours. MeOH (30 mL), CHCl$_3$ (300 mL), and a saturated aqueous NaHCO$_3$ solution (100 mL) were added, and the organic layer was separated. Washing was performed with saturated aqueous NaHCO$_3$ solutions (3×100 mL), and the collected washing liquid was extracted with CHCl$_3$ (100 mL). The collected organic layer was dried over anhydrous Na$_2$SO$_4$, filtered, and concentrated under reduced pressure. The residue was separated and purified by silica gel column chromatography [neutral silica gel, CH$_2$Cl$_2$-MeOH-pyridine (99:0.5:0.5 to 94.5:5:0.5, v/v)] to recover a fraction containing 9b. The solvent was removed under reduced pressure to give 9b (3.47 g, 5 mmol, 71%) as a colorless foamed material.

$^1$H NMR (300 MHz, CDCl$_3$) (8.25 (d, 1H), 7.44-7.39 (m, 3H), 7.34-7.22 (m, 9H), 7.02 (d, 1H), 6.92-6.84 (m, 6H), 6.25 (t, 1H), 5.13 (s, 2H), 4.47 (br, 1H), 4.09 (q, 1H), 3.80 (s, 9H), 3.55-3.39 (m, 2H), 2.71-2.62 (m, 1H), 2.30-2.22 (m, 1H). FAB-HRMS: Calcd. for [M+H]$^+$; 694.2765. Found; 694.2763.

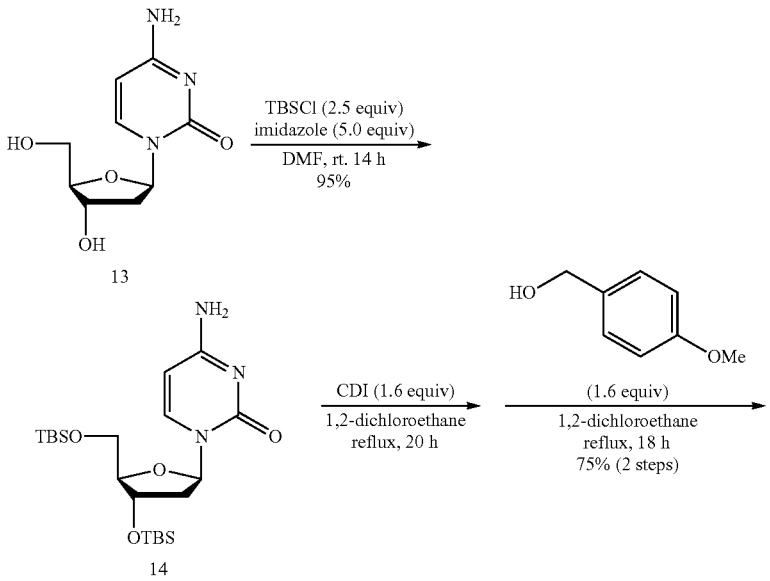

-continued

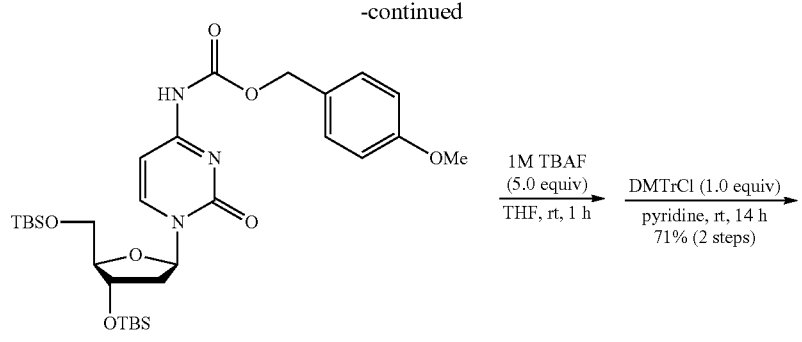

15

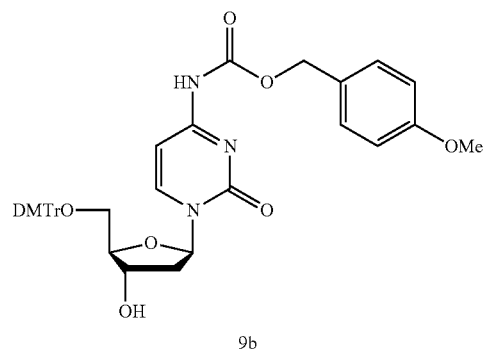

9b

Synthesis of 3',5'-O-bis(TBS)-2'-deoxyadenosine [11]

Synthesis was performed according to the method described in the literature, using 2'-deoxyadenosine (10) as a starting material. $^1$H NMR spectrum was consistent with the literature value.

Synthesis of 3',5'-O-bis(TBS)-N$^6$-MCbz-2'-deoxyadenosine [12]

3',5'-O-bis(TBS)-2'-deoxyadenosine (11) (7.19 g, 15 mmol) was repeatedly azeotropically dried with pyridine, toluene, and CHCl$_3$ to form a 1,2-dichloroethane solution (150 mL), CDI (3.89 g, 24 mmol) was added, and heated to reflux for 17 hours. 4-methoxybenzylalcohol (3.00 mL, 24 mmol) was added thereto, and heated to reflux for further 20 hours. A saturated aqueous NaHCO$_3$ solution (100 mL) was added thereto, and the organic layer was separated. Washing was performed with saturated aqueous NaHCO$_3$ solutions (3×100 mL), and the collected washing liquid was extracted with CH$_2$Cl$_2$ (100 mL). The collected organic layer was dried over anhydrous Na$_2$SO$_4$, filtered, and concentrated under reduced pressure. The residue was separated and purified by silica gel column chromatography [neutral silica gel, hexane-AcOEt (2:1, v/v)] to recover a fraction containing 12. The solvent was removed under reduced pressure to give 12 (7.26 g, 11 mmol, 75%) as a colorless foamed material.

$^1$H NMR (400 MHz, CDCl$_3$) δ8.75 (s, 1H), 8.41 (s, 1H), 8.26 (s, 1H), 8.38 (d, 2H), 6.90 (d, 2H), 6.49 (t, 1H), 5.23 (s, 2H), 4.63-4.59 (m, 1H), 4.04 (q, 1H), 3.89-3.75 (m, 5H), 2.67-2.61 (m, 1H), 2.48-2.42 (m, 1H), 0.92-0.87 (m, 18H), 0.10-0.04 (m, 12H). FAB-HRMS: Calcd. for [M+H]$^+$; 644.3300. Found; 644.3298.

Synthesis of N$^6$-MCbz-5'-O-DMTr-2'-deoxyadenosine [9c]

3',5'-O-bis(TBS)-N$^6$-MCbz-2'-deoxyadenosine (12) (7.26 g, 11 mmol) was dissolved into THF (55 mL), 1 M TBAF/THF (55 mL) was added thereto, and stirring was performed at room temperature for 1 hour. A saturated aqueous NaHCO$_3$ solution (100 mL) and AcOEt (300 mL) were added, and the organic layer was separated. Washing was performed with saturated aqueous NaHCO$_3$ solutions (3×100 mL), and the collected washing liquid was extracted with AcOEt (100 mL). The collected organic layer was dried over anhydrous Na$_2$SO$_4$, filtered, and concentrated under reduced pressure. To the residue, pyridine (110 mL) and DMTrCl (4.48 g, 13.2 mmol) were added, and stirred at room temperature for 18 hours. MeOH (50 mL), CHCl$_3$ (300 mL), and a saturated aqueous NaHCO$_3$ solution (100 mL) were added, and the organic layer was separated. Washing was performed with a saturated aqueous NaHCO$_3$ solution (3×100 mL), and the collected washing liquid was extracted with CHCl$_3$ (100 mL). The collected organic layer was dried over anhydrous Na$_2$SO$_4$, filtered, and concentrated under reduced pressure. The residue was separated and purified by silica gel column chromatography [neutral silica gel, CH$_2$Cl$_2$-MeOH-pyridine (98:1.5:0.5 to 96.5:3:0.5, v/v)] to recover a fraction containing 9c. The solvent was removed under reduced pressure to give 9c (5.08 g, 7 mmol, 64%) as a colorless foamed material.

$^1$H NMR (300 MHz, CDCl$_3$) δ8.68 (s, 1H), 8.16 (br, 1H), 8.06 (s, 1H), 7.40-7.36 (m, 2H), 7.31-7.16 (m, 9H), 6.91-6.77 (m, 6H), 6.46 (t, 1H), 5.23 (s, 2H), 4.70 (br, 1H), 4.16 (q, 1H), 3.77 (s, 9H), 3.41-3.39 (m, 2H), 2.91-2.82 (m, 1H), 2.59-2.51 (m, 1H), 1.65 (br, 1H). FAB-HRMS: Calcd. for [M+H]$^+$; 718.2877. Found; 718.2880.

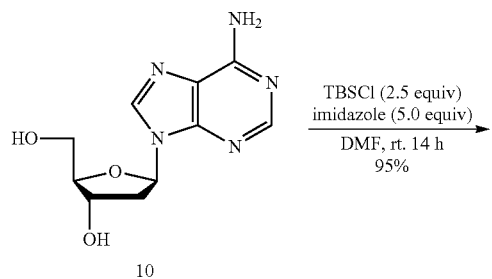
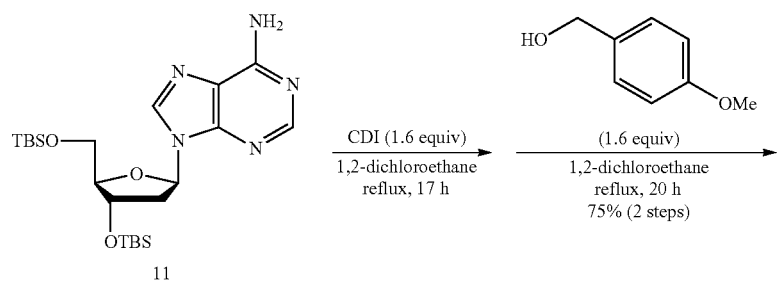
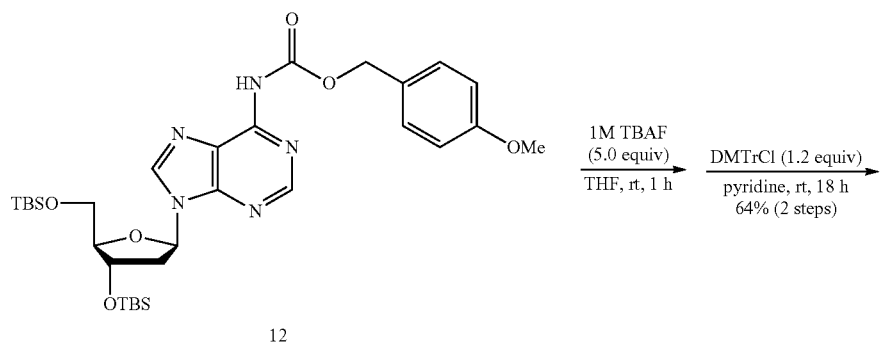
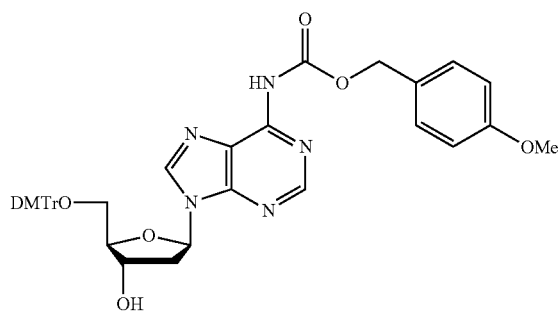

Synthesis of O^6-Tse-5'-O-DMTr-2'-deoxyguanosine [9d]

Synthesis was performed according to the method described in the literature, using 2'-deoxyguanosine (1) as a starting material. $^1$H NMR spectrum was consistent with the literature value.

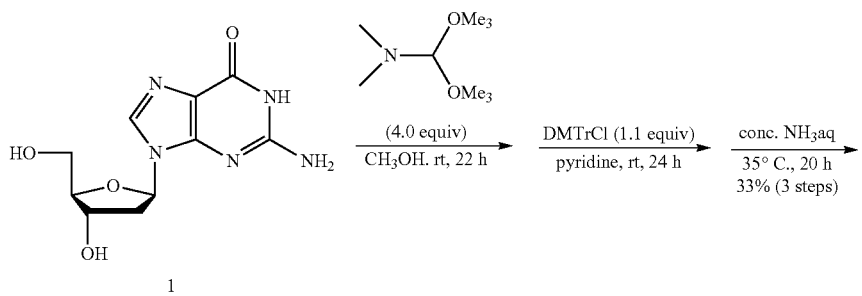

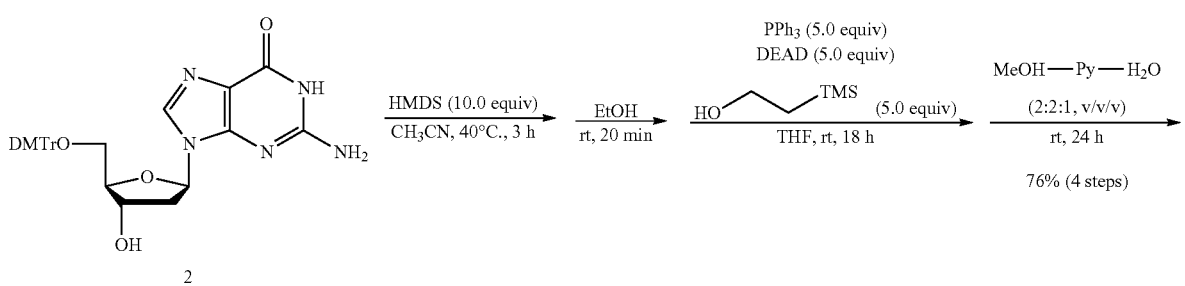

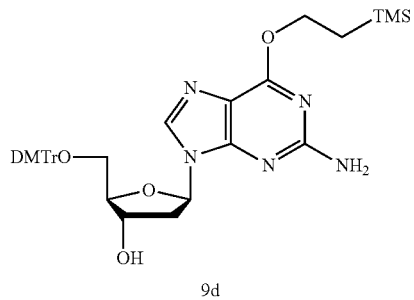

Synthesis of 3',5'-bis-O-benzoyl-N$^2$-MCbz-deoxyguanosine [6]

3',5'-bis-O-benzoyldeoxyguanosine (4) (0.52 g, 1.09 mmol) was dissolved in THF (13.0 mL), DIPEA (0.95 mL, 5.5 mmol) and TMSCI (0.15 mL, 1.0 mmol) were added thereto, and stirring was performed at room temperature for 1 hour. Triphosgene (0.1 g, 0.35 mmol) was added and stirred at 0° C. for 1 hour. 4-methoxybenzylalcohol (0.17 g, 1.2 mmol) was added at room temperature, and heated to reflux overnight. Washing was performed with saturated saline solutions (3×10 mL), and the collected washing liquid was extracted with CH$_2$Cl$_2$ (5 mL). The collected organic layer was dried over anhydrous Na$_2$SO$_4$, filtered, and concentrated under reduced pressure. The residue was separated and purified by silica column chromatography [neutral silica gel, CH$_2$Cl$_2$-MeOH-pyridine (99:0.5:0.5 to 94.5:5:0.5, v/v)] to recover a fraction containing 6. The solvent was removed under reduced pressure to give 6 (0.09 g, 0.40 mmol, 37%) as a yellow foamed material.

$^1$H NMR (300 MHz, CDCl$_3$) δ 11.31 (s, 1H), 8.35 (s, 1H), 8.06-8.04 (d, J=7.5 Hz, 2H), 7.96-7.93 (d, J=7.2 Hz, 2H), 7.72 (s, 1H), 7.64-7.59 (m, 1H), 7.55-7.45 (m, 9H), 7.39-7.34 (m, 4H), 6.94-6.92 (m, 2H), 6.30-6.26 (t, J=7.2, 6.6 Hz, 1H), 5.80-5.78 (m, 1H), 5.23 (s, 2H), 4.94-4.90 (m, 1H), 4.75-4.69 (m, 1H), 4.69-4.67 (m, 1H), 3.83 (s, 1H), 3.17-3.07 (m, 1H), 2.70-2.65 (m, 1H).

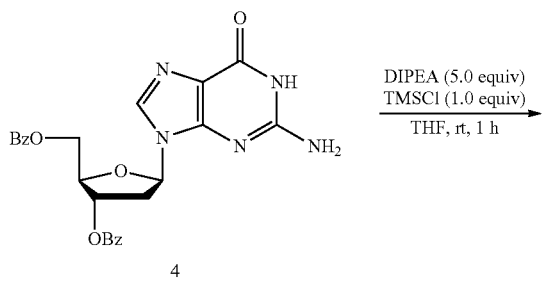

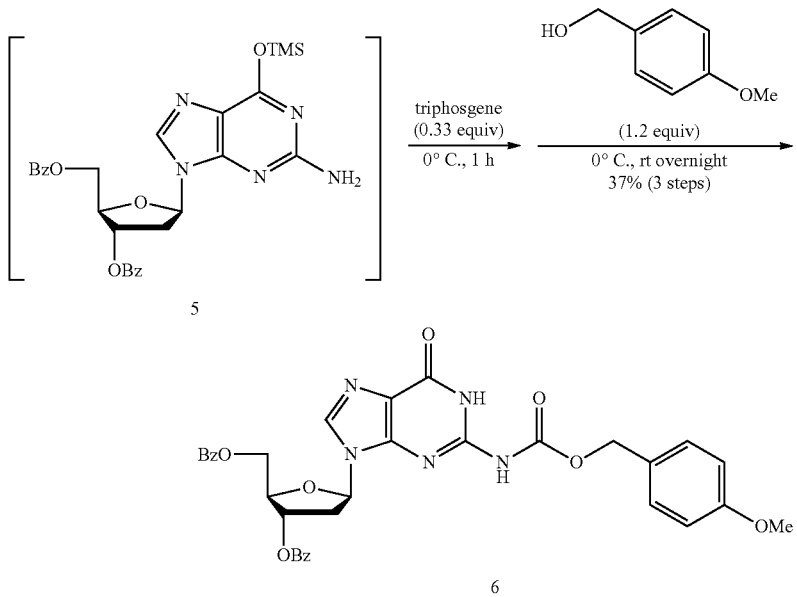

Synthesis of 2-chloro-1,3,2-oxazaphospholidine [(4S,5R)-18]

(αR,2S)-7 (1.07 g, 5.16 mmol) was repeatedly azeotropically dried with toluene, then dissolved in toluene (3 mL), and N-methylmorpholine (1.13 mL, 10.32 mmol) was added thereto. The mixed solution was slowly added to a solution of phosphorus trichloride (0.45 mL, 5.16 mmol) in toluene (2.5 mL) at 0° C. with a syringe. The reaction mixture was stirred at room temperature for 2 hours, and the resulting salt was filtered off at −78° C. under an Ar atmosphere and concentrated under reduced pressure under an Ar atmosphere to give 2-chloro-1,3,2-oxazaphospholidine (4S,5R)-18 (1.28 g, 4.71 mmol). Light yellow oil. (4S,5R)-18 was used for the reaction, without further purification.

Synthesis of [(4R,5S)-18]

Synthesis was performed in the same manner as (4S,5R)-18, using (αS,2R)-7 as a starting material.

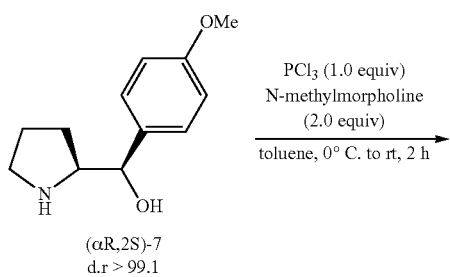

-continued

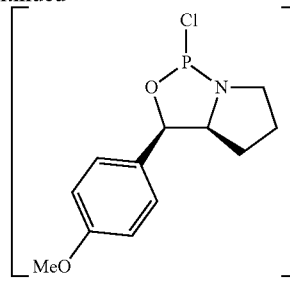

(4S,5R)-18

Synthesis of oxazaphospholidine monomer [(Rp)-20a]

5′-O-(DMTr)thymidine (9a) (0.86 g, 1.58 mmol) was repeatedly azeotropically dried with pyridine, toluene and THF, then dissolved in THF (8 mL), and Et₃N (1.52 mL, 11 mmol) was added thereto. The mixed solution was cooled to −78° C. and a solution of 0.5 M (4S,5R)-18 in THF (9.5 mL, 4.75 mmol) was slowly added thereto with a syringe. The reaction solution was stirred at room temperature for 2 hours, and CHCl₃ (300 mL) and a saturated aqueous NaHCO₃ solution (100 mL) was added thereto. The organic layer was separated and washed with saturated aqueous NaHCO₃ solutions (2×100 mL), and the collected washing liquid was extracted with CHCl₃ (100 mL). The collected organic phase was dried over anhydrous Na₂SO₄, filtered, and concentrated under reduced pressure. The residue was separated and purified by silica gel column chromatography

[NH-silica gel, toluene-AcOEt (7:3, v/v), Et$_3$N 0.1%], a fraction containing (Rp)-20a was collected, and the solvent was removed under reduced pressure to give (Rp)-20a (0.53 g, 0.68 mmol, 43%) as a colorless foamed material.

$^1$H NMR (400 MHz, CDCl$_3$) δ7.60 (s, 1H), 7.41-7.22 (m, 11H), 6.89-6.79 (m, 6H), 6.43 (t, 1H), 5.68 (d, 1H), 4.94-4.89 (m, 1H), 4.13 (q, 1H), 3.80-3.77 (m, 10H), 3.60-3.53 (m, 1H), 3.49-3.36 (m, 2H), 3.20-3.13 (m, 1H), 2.60-2.55 (m, 1H), 2.40-2.33 (m, 1H), 1.66-1.58 (m, 2H), 1.42 (s, 3H), 1.21-1.14 (m, 1H), 1.00-0.91 (m, 1H). $^{31}$P NMR (161 MHz, CDCl$_3$) b 155.65. FAB-HRMS: Calcd. for [M+Na]$^+$; 802.2869. Found; 802.2866.

The crude products of (Rp)-20b-d and (Sp)-20a-d were all obtained by the same method as described above. Only the conditions for silica gel column chromatography are shown for these compounds.

Synthesis of oxazaphospholidine monomer [(Rp)-20b]

The crude product of (Rp)-20b was obtained from 9b (1.02 g, 1.47 mmol) and (4S,5R)-18 (0.80 g, 2.94 mmol), by the same method as (Rp)-20a. Purification was performed by silica gel column chromatography [NH-silica gel, toluene-AcOEt (7:3, v/v), Et$_3$N 0.1%] to give (Rp)-20b (0.65 g, 0.70 mmol, 47%) as a colorless foamed material.

$^1$H NMR (400 MHz, CDCl$_3$) δ8.25 (d, 1H), 7.39-7.13 (m, 13H), 6.91-6.79 (m, 8H), 6.26 (t, 1H), 5.68 (d, 1H), 5.13 (s, 2H), 4.87-4.81 (m, 1H), 4.16 (q, 1H), 3.83-3.76 (m, 14H), 3.60-3.52 (m, 1H), 3.47 (d, 2H), 3.22-3.13 (m, 1H), 2.82-2.75 (m, 1H), 2.38-2.32 (m, 1H), 1.67-1.57 (m, 2H), 1.22-1.15 (m, 1H), 1.01-0.94 (m, 1H). $^{31}$P NMR (161 MHz, CDCl$_3$) b 156.72. FAB-HRMS: Calcd. for [M+H]$^+$; 929.3527. Found; 929.3528.

Synthesis of oxazaphospholidine monomer [(Rp)-20c]

The crude product of (Rp)-20c was obtained from 9c (1.05 g, 1.47 mmol) and (4S,5R)-18 (0.80 g, 2.94 mmol), by the same method as (Rp)-20a. Purification was performed by silica gel column chromatography [NH-silica gel, toluene-AcOEt (8:2, v/v), Et$_3$N 0.1%] to give (Rp)-20c (0.62 g, 0.65 mmol, 44%) as a colorless foamed material.

$^1$H NMR (400 MHz, CDCl$_3$) δ8.67 (s, 1H), 8.30 (br, 1H), 8.06 (s, 1H), 7.38-7.35 (m, 4H), 7.29-7.14 (m, 9H), 6.91-6.86 (m, 4H), 6.75-6.70 (m, 4H), 6.47 (t, 1H), 5.77 (d, 1H), 5.22 (s, 2H), 5.09-5.03 (m, 1H), 4.29 (q, 1H), 3.88-3.84 (m, 1H), 3.81 (s, 6H), 3.74 (s, 6H), 3.62-3.54 (m, 1H), 3.41-3.33 (m, 2H), 3.20-3.11 (m, 1H), 2.99-2.92 (m, 1H), 2.71-2.65 (m, 1H), 1.68-1.59 (m, 2H), 1.26-1.16 (m, 1H), 1.03-0.94 (m, 1H). $^{31}$P NMR (161 MHz, CDCl$_3$) b 154.97. FAB-HRMS: Calcd. for [M+Na]$^+$; 975.3458. Found; 975.3459.

Synthesis of oxazaphospholidine monomer [(Rp)-20d]

The crude product of (Rp)-20d was obtained from 9d (0.67 g, 1.00 mmol) and (4S,5R)-18 (1.07 g, 3.95 mmol), by the same method as (Rp)-20a. Purification was performed by silica gel column chromatography [NH-silica gel, toluene-AcOEt (9:1, v/v), Et$_3$N 0.1%] to give (Rp)-20d (0.34 g, 0.38 mmol, 38%) as a colorless foamed material.

$^1$H NMR (400 MHz, CDCl$_3$) δ7.69 (s, 1H), 7.43-7.13 (m, 11H), 6.92-6.74 (m, 6H), 6.33 (t, 1H), 5.75 (d, 1H), 5.04 (m, 1H), 4.65-4.53 (m, 4H), 4.26 (q, 1H), 3.92-3.74 (m, 10H), 3.64-3.53 (m, 1H), 3.41-3.30 (m, 2H), 3.20-3.13 (m, 1H), 2.57-2.55 (m, 1H), 2.24-2.19 (m, 1H), 1.68-1.55 (m, 2H), 1.26-1.12 (m, 3H), 1.03-0.96 (m, 1H), 0.08 (s, 9H). $^{31}$P NMR (161 MHz, CDCl$_3$) b 155.04. FAB-HRMS: Calcd. for [M+H]$^+$; 905.3823. Found; 905.3826.

[Oxazaphospholidine monomer [(Sp)-20a]]

The crude product of (Sp)-20a was obtained from 9a (0.85 g, 1.57 mmol) and (4R,5S)-18 (1.28 g, 4.71 mmol), by the same method as (Rp)-20a. Purification was performed by silica gel column chromatography [NH-silica gel, toluene-AcOEt (7:3, v/v), Et$_3$N 0.1%] to give (Sp)-20a (0.82 g, 1.05 mmol, 67%) as a colorless foamed material.

$^1$H NMR (400 MHz, CDCl$_3$) δ8.02 (br, 1H), 7.64 (s, 1H), 7.42-7.16 (m, 11H), 6.90-6.82 (m, 6H), 6.41 (t, 1H), 5.63 (d, 1H), 4.94-4.89 (m, 1H), 4.18 (q, 1H), 3.86-3.76 (m, 10H), 3.56-3.48 (m, 1H), 3.39-3.34 (m, 2H), 3.20-3.13 (m, 1H), 2.50-2.43 (m, 1H), 2.39-2.31 (m, 1H), 1.64-1.59 (m, 2H), 1.40 (s, 3H), 1.25-1.19 (m, 1H), 1.06-0.90 (m, 1H). $^{31}$P NMR (161 MHz, CDCl$_3$) b 156.12. FAB-HRMS: Calcd. for [M+Na]$^+$; 802.2869. Found; 802.2874.

Synthesis of oxazaphospholidine monomer [(Sp)-20b]

The crude product of (Sp)-20b was obtained from 9b (1.01 g, 1.46 mmol) and (4R,5S)-18 (1.00 g, 3.67 mmol), by the same method as (Rp)-20a. Purification was performed by silica gel column chromatography [NH-silica gel, toluene-AcOEt (7:3, v/v), Et$_3$N 0.1%] to give (Sp)-20b (0.55 g, 0.59 mmol, 40%) as a colorless foamed material.

$^1$H NMR (400 MHz, CDCl$_3$) δ8.36 (d, 1H), 7.43-7.16 (m, 13H), 6.94-6.84 (m, 8H), 6.24 (t, 1H), 5.68 (d, 1H), 5.13 (s, 2H), 4.90-4.83 (m, 1H), 4.18 (q, 1H), 3.87-3.76 (m, 14H), 3.57-3.44 (m, 3H), 3.21-3.13 (m, 1H), 2.69-2.63 (m, 1H), 2.41-2.32 (m, 1H), 1.69-1.60 (m, 2H), 1.25-1.17 (m, 1H), 1.04-0.95 (m, 1H). $^{31}$P NMR (161 MHz, CDCl$_3$) b 155.97. FAB-HRMS: Calcd. for [M+Na]$^+$; 951.3346. Found; 951.3349.

Synthesis of oxazaphospholidine monomer [(Sp)-20c]

The crude product of (Sp)-20c was obtained from 9c (1.05 g, 1.46 mmol) and (4R,5S)-18 (1.00 g, 3.67 mmol), by the same method as (Rp)-20a. Purification was performed by silica gel column chromatography [NH-silica gel, toluene-AcOEt (8:2, v/v), Et$_3$N 0.1%] to give (Sp)-20c (0.67 g, 0.70 mmol, 48%) as a colorless foamed material.

$^1$H NMR (400 MHz, CDCl$_3$) δ8.67 (s, 1H), 8.29 (br, 1H), 8.11 (s, 1H), 7.41-7.35 (m, 4H), 7.30-7.12 (m, 9H), 6.91-6.74 (m, 8H), 6.46 (t, 1H), 5.72 (d, 1H), 5.22 (s, 2H), 5.06-5.00 (m, 1H), 4.34 (q, 1H), 3.91-3.85 (m, 1H), 3.80 (s, 6H), 3.76 (s, 6H), 3.62-3.52 (m, 1H), 3.48-3.34 (m, 2H), 3.22-3.13 (m, 1H), 2.94-2.88 (m, 1H), 2.63-2.58 (m, 1H), 1.69-1.58 (m, 2H), 1.26-1.19 (m, 1H), 1.06-0.98 (m, 1H). $^{31}$P NMR (161 MHz, CDCl$_3$) b 155.36. FAB-HRMS: Calcd. for [M+H]$^+$; 953.3639. Found; 953.3643.

Synthesis of oxazaphospholidine monomer [(Sp)-20d]

The crude product of (Sp)-20d was obtained from 9d (0.67 g, 1.00 mmol) and (4R,5S)-18 (1.07 g, 3.95 mmol), by the same method as (Rp)-20a. Purification was performed by silica gel column chromatography [NH-silica gel, toluene-AcOEt (9:1, v/v), Et$_3$N 0.1%] to give (Sp)-20d (0.34 g, 0.38 mmol, 38%) as a colorless foamed material.

$^1$H NMR (400 MHz, CDCl$_3$) δ7.73 (s, 1H), 7.44-7.13 (m, 11H), 6.88-6.78 (m, 6H), 6.30 (t, 1H), 5.71 (d, 1H), 5.01 (m, 1H), 4.61-4.53 (m, 4H), 4.30 (q, 1H), 3.90-3.77 (m, 10H), 3.62-3.52 (m, 1H), 3.46-3.42 (m, 1H), 3.33-3.30 (m, 1H), 3.22-3.13 (m, 1H), 2.52-2.48 (m, 1H), 2.25-2.20 (m, 1H), 1.66-1.59 (m, 2H), 1.26-1.19 (m, 3H), 1.07-0.98 (m, 1H), 0.08 (s, 9H). $^{31}$P NMR (161 MHz, CDCl$_3$) b 155.36. FAB-HRMS: Calcd. for [M+H]$^+$; 905.3823. Found; 905.3825.

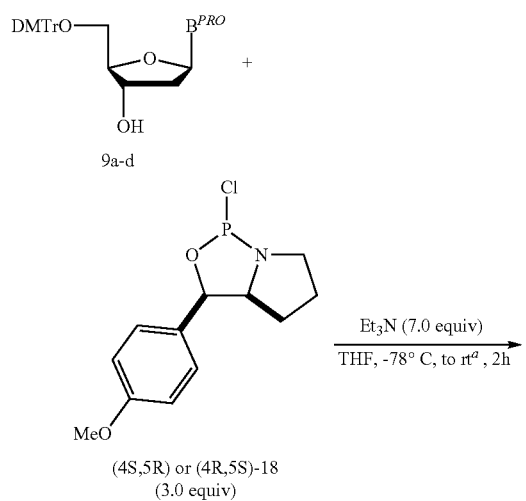

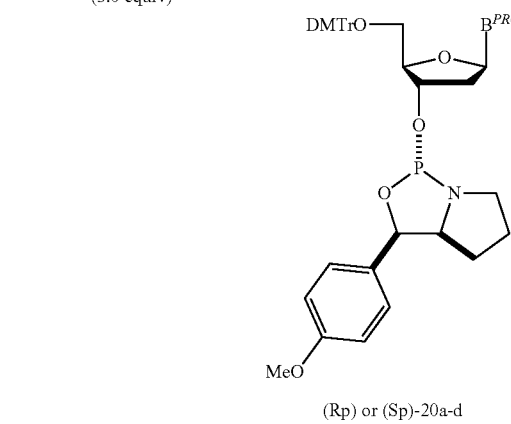

9a to 9d (base protected by a protecting group), Compound 18 used for synthesis of each monomer, a yield of each monomer, and a mass ratio of an Rp isomer and a Sp isomer contained in the obtained monomer are described in Table 1.

In Table 1, Th represents thymine, $Cy^{MCbz}$ represents cytosine of which the amino group is protected by an MCbz group, $Ad^{MCbz}$ represents adenine of which the amino group is protected by an MCbz group, and $Gu^{Tse}$ represents guanine of which the amino group is protected by a trimethylsilyl group, respectively.

TABLE 1

| | 9a to 9d | | | 20 | |
|---|---|---|---|---|---|
| Entry | Used compound | Included base | 18 | Yield (%) | Rp:Sp[b] |
| 1 | 9a | Th | (4S,5R) | 43 | >99:1 |
| 2 | 9b | $Cy^{MCbz}$ | (4S,5R) | 47 | >99:1 |
| 3 | 9c | $Ad^{MCbz}$ | (4S,5R) | 44 | >99:1 |
| 4 | 9d | $Gu^{Tse}$ | (4S,5R) | 37 | >99:1 |
| 5 | 9a | Th | (4R,5S) | 67 | >1:99 |
| 6 | 9b | $Cy^{MCbz}$ | (4R,5S) | 40 | >1:99 |
| 7 | 9c | $Ad^{MCbz}$ | (4R,5S) | 48 | >1:99 |
| 8 | 9d | $Gu^{Tse}$ | (4R,5S) | 38 | >1:99 |

[a] In entries 4 to 8, a processing condition by Et₃N described above was at −78° C.
[b] 31P NMR was used for measurement.

<Synthesis 1 of Boranophosphate DNA>

Manual solid phase synthesis of boranophosphate DNA (PB-DNA) (24a-d,25,26) was performed using a controlled-pore glass (CPG) as a solid support and a glass filter (10 mm×50 mm) having a cock at the bottom as a reaction vessel.

First, 5'-O-(DMTr)thymidine (27) supported on CPG via succinyl linker was treated with 1% TFA/CH₂Cl₂ (4×5 s) to remove a 5'-O-DMTr group, and the following steps (i) to (v) were performed to synthesize H-phosphonate DNA (23).
 (i) washing (CH₂Cl₂, CH₃CN)
 (ii) coupling (0.2M monomer 20a-d and 1.0M CMPT(21) in CH₃CN;5 min),
 (iii) washing (CH₃CN, CH₂Cl₂)
 (iv) 1% TFA/CH₂Cl₂-Et₃SiH (1:1,v/v)(4×1 min)
 (v) washing (CH₂Cl₂, CH₃CN)

Subsequently, DMAc (0.8 mL), BSA (0.1 mL), and BH₃·SMe2 (0.1 mL) were added to the synthesized 23 at room temperature. After 15 minutes, the reaction solution was removed and CPG was washed with DMAc and CH₃CN. CPG was treated with concentrated aqueous NH₃ solution-EtOH (3:1, v/v) at 25° C. for 3 hours or 55° C. for 12 hours, CPG was filtered off, and the filtrate was concentrated under reduced pressure. The residue was analyzed and identified by RP-HPLC and ESI-MS.

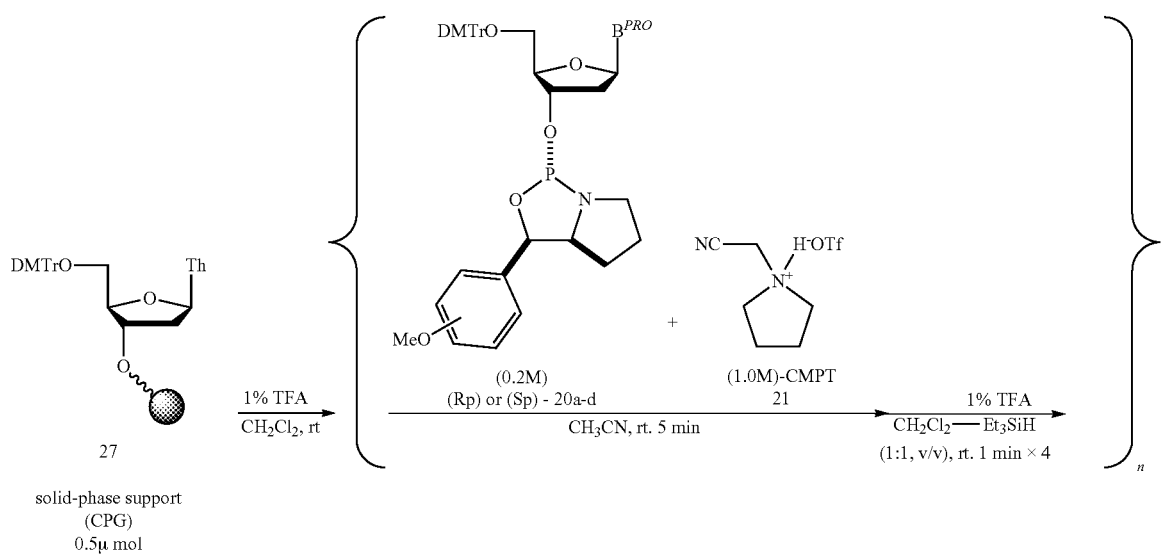

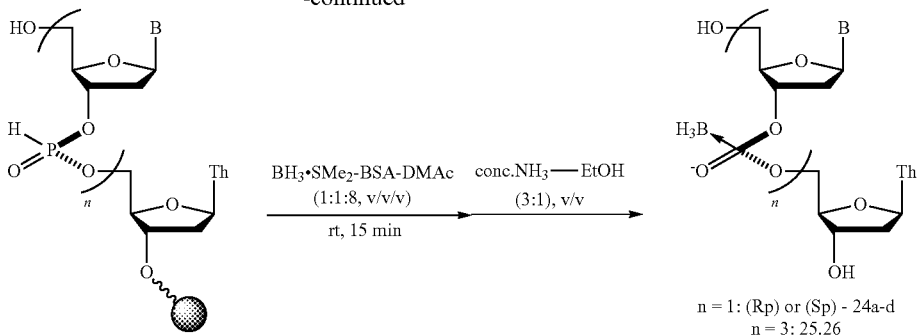

BPRO = Th, Cy$^{MCbz}$, Ad$^{MCbz}$, Gu$^{Tse}$

A sequence of the obtained boranophosphate DNA (PB-DNA), reaction conditions for release of the oligomer from a solid support (temperature and retention time under a condition of conc. NH$_3$-EtOH (3:1, v/v)), a yield, and a stereochemical purity of a dimer are listed in Table 2, respectively. In addition, in Table 2, description of Rp or Sp indicates whether the absolute configuration of a boranophosphate structure in the oligomer is Sp or Rp. The description of all-(Rp) indicates that the absolute configuration of a boranophosphate structure in the oligomer is all Rp, and the description of all-(Sp) indicates that the absolute configuration of a boranophosphate structure in the oligomer is all Sp, respectively.

TABLE 2

| Entry | Sequence of PB-DNA[a] | | Conditions for release of the oligomer from solid support | Yield (%)[b] | Stereochemical purity[b] |
|---|---|---|---|---|---|
| 1 | (Rp)-24a | (Rp)-T$_B$T | 25° C., 3 h | 91 | 98:2 |
| 2 | (Rp)-24b | (Rp)-dC$_B$T | 25° C., 3 h | 91 | >99:1 |
| 3 | (Rp)-24c | (Rp)-dA$_B$T | 25° C., 3 h | — | >99:1 |
| 4 | (Rp)-24c | (Rp)-dA$_B$T | 55° C., 12 h | 88 | >99:1 |
| 5 | (Rp)-24d | (Rp)-dG$_B$T | 55° C., 12 h | 77 | >99:1 |
| 6 | (Sp)-24a | (Sp)-T$_B$T | 25° C., 3 h | 88 | >99:1 |
| 7 | (Sp)-24b | (Sp)-dC$_B$T | 25° C., 3 h | 93 | 98:2 |
| 8 | (Sp)-24c | (Sp)-dA$_B$T | 25° C., 3 h | — | >99:1 |
| 9 | (Sp)-24c | (Sp)-dA$_B$T | 55° C., 12 h | 87 | >99:1 |
| 10 | (Sp)-24d | (Sp)-dG$_B$T | 55° C., 12 h | 77 | 97:3 |
| 11 | 25 | all-(Rp)-d(C$_B$A$_B$G$_B$T) | 55° C., 12 h | 14[c] | — |
| 12 | 26 | all-(Sp)-d(C$_B$A$_B$G$_B$T) | 55° C., 12 h | 23[c] | — |

[a]"B" represents being bonded by a boranophosphate structure.
[b]Calculated by reverse phase HPLC. The HPLC charts are shown in FIGS. 1 to 7.
[c]Isolated yield FIG. 1 is HPLC charts showing results of reverse phase HPLC of (A) a synthesis reaction solution (crude) of (Rp)-T$_B$T [(Rp)-24a] and (B) a synthesis reaction solution (crude) of (Sp)-T$_B$T [(Sp)-24a].

The measurement conditions of the reverse phase HPLC were as follows.

Gradient cycle: After a linear gradient of acetonitrile from 0% to 10% for 30 minutes in a 0.1 M triethylammonium buffer solution (pH 7.0), acetonitrile was held at 10% for 30 minutes.

Measurement temperature: 30° C.

Flow rate: 0.5 mL/min

Column: μBondasphere 5 μm C18 column (100 Å, 3.9 mm×150 mm) (Waters)

Figure 2:
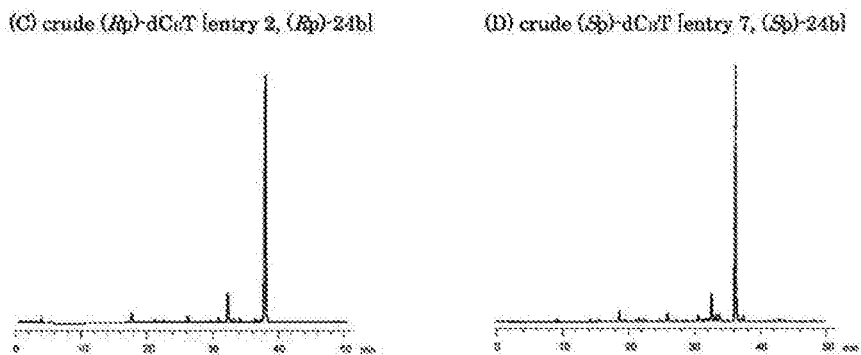
FIG. 2 shows HPLC charts showing results of reverse phase HPLC of (C) a synthesis reaction solution (crude) of (Rp)-$dC_BT$ [(Rp)-24b] and (D) a synthesis reaction solution (crude) of (Sp)-$dC_BT$ [(Sp)-24b].

FIG. 2 is HPLC charts showing results of reverse phase HPLC of (C) a synthesis reaction solution (crude) of (Rp)-dC$_B$T [(Rp)-24b] and (D) a synthesis reaction solution (crude) of (Sp)-dC$_B$T [(Sp)-24b].

The measurement conditions of the reverse phase HPLC were as follows.

Gradient cycle: After a linear gradient of acetonitrile from 0% to 10% for 30 minutes in a 0.1 M triethylammonium buffer solution (pH 7.0), acetonitrile was held at 10% for 20 minutes.

Measurement temperature: 30° C.

Flow rate: 0.5 mL/min

Column: μBondasphere 5 μm C18 column (100 Å, 3.9 mm×150 mm) (Waters)

Figure 3:
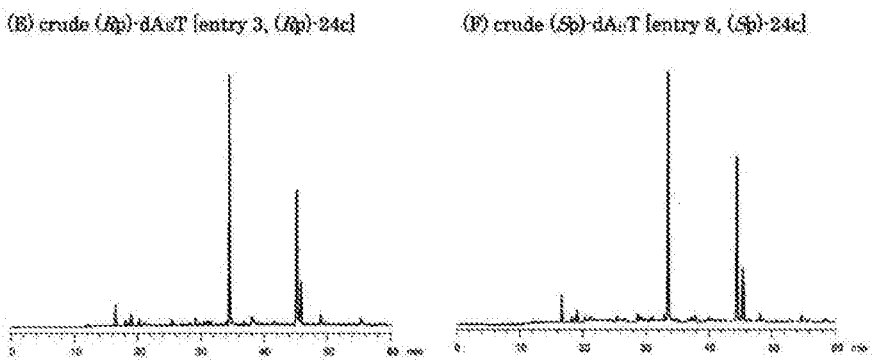
FIG. 3 shows is HPLC charts showing results of reverse phase HPLC of (E) a synthesis reaction solution (crude) of (Rp)-$dA_BT$ [(Rp)-24c] and (D) a synthesis reaction solution (crude) of (Sp)-$dA_BT$ [(Sp)-24c].

FIG. 3 is HPLC charts showing results of reverse phase HPLC of (E) a synthesis reaction solution (crude) of (Rp)-dA$_B$T [(Rp)-24c] and (D) a synthesis reaction solution (crude) of (Sp)-dA$_B$T [(Sp)-24c].

The measurement conditions of the reverse phase HPLC were as follows.

Gradient cycle: A linear gradient of acetonitrile from 0% to 30% for 60 minutes in a 0.1 M triethylammonium buffer solution (pH 7.0).

Measurement temperature: 30° C.

Flow rate: 0.5 mL/min

Column: μBondasphere 5 μm C18 column (100 Å, 3.9 mm×150 mm) (Waters)

Figure 4:
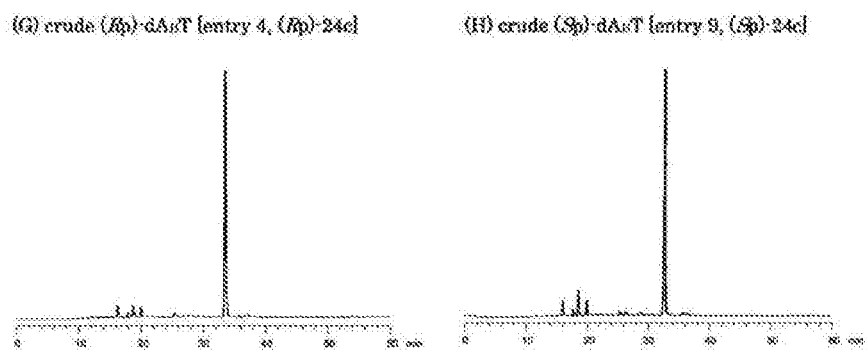
FIG. 4 shows HPLC charts showing results of reverse phase HPLC of (G) a synthesis reaction solution (crude) of (Rp)-$dA_BT$ [(Rp)-24c] and (H) a synthesis reaction solution (crude) of (Sp)-$dA_BT$ [(Sp)-24c].

FIG. 4 is HPLC charts showing results of reverse phase HPLC of (G) a synthesis reaction solution (crude) of (Rp)-dA$_B$T [(Rp)-24c] and (H) a synthesis reaction solution (crude) of (Sp)-dA$_B$T [(Sp)-24c].

The measurement conditions of the reverse phase HPLC were as follows.

Gradient cycle: A linear gradient of acetonitrile from 0% to 30% for 60 minutes in a 0.1 M triethylammonium buffer solution (pH 7.0).

Measurement temperature: 30° C.

Flow rate: 0.5 mL/min

Column: μBondasphere 5 μm C18 column (100 Å, 3.9 mm×150 mm) (Waters)

Figure 5:
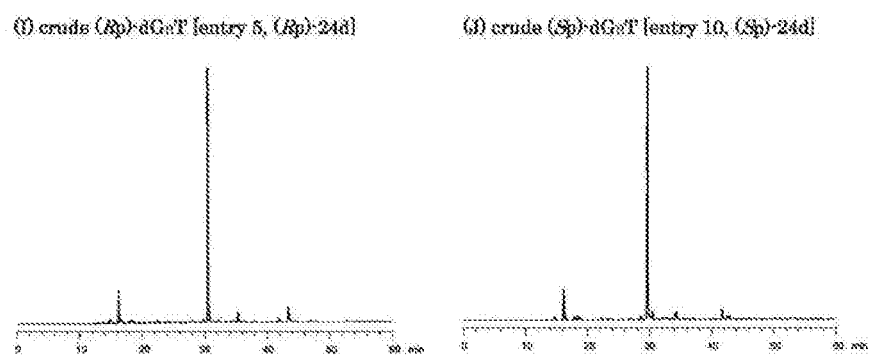
FIG. 5 shows HPLC charts showing results of reverse phase HPLC of (I) a synthesis reaction solution (crude) of (Rp)-$dG_BT$ [(Rp)-24d] and (J) a synthesis reaction solution (crude) of (Sp)-$dG_BT$ [(Sp)-24d].

FIG. 5 is HPLC charts showing results of reverse phase HPLC of (I) a synthesis reaction solution (crude) of (Rp)-dG$_B$T [(Rp)-24d] and (J) a synthesis reaction solution (crude) of (Sp)-dG$_B$T [(Sp)-24d].

The measurement conditions of the reverse phase HPLC were as follows.

Gradient cycle: A linear gradient of acetonitrile from 0% to 30% for 60 minutes in a 0.1 M triethylammonium buffer solution (pH 7.0).

Measurement temperature: 30° C.

Flow rate: 0.5 mL/min

Column: μBondasphere 5 μm C18 column (100 Å, 3.9 mm×150 mm) (Waters)

Figure 6:
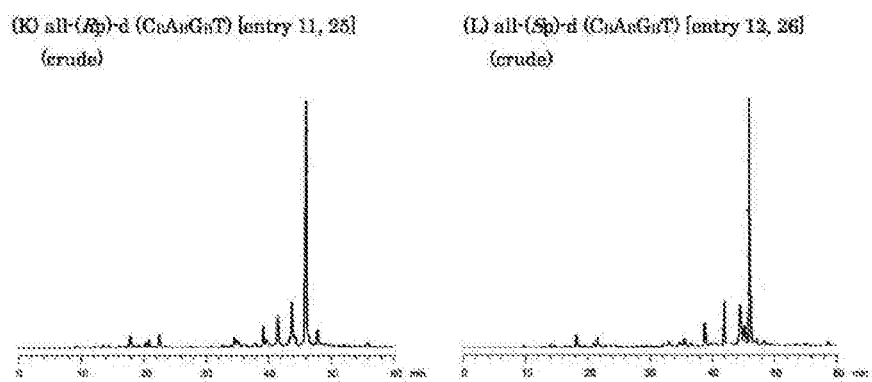
FIG. 6 shows HPLC charts showing results of reverse phase HPLC of (K) a synthesis reaction solution (crude) of all-(Rp)-d ($C_BA_BG_BT$) [25] and (L) a synthesis reaction solution (crude) of all-(Sp)-d ($C_BA_BG_BT$) [26].

FIG. 6 is HPLC charts showing results of reverse phase HPLC of (K) a synthesis reaction solution (crude) of all-(Rp)-d (C$_B$A$_B$G$_B$T) [25] and (L) a synthesis reaction solution (crude) of all-(Sp)-d (C$_B$A$_B$G$_B$T) [26].

The measurement conditions of the reverse phase HPLC were as follows.

Gradient cycle: A linear gradient of acetonitrile from 0% to 20% for 60 minutes in a 0.1 M triethylammonium buffer solution (pH 7.0).

Measurement temperature: 30° C.

Flow rate: 0.5 mL/min

Column: μBondasphere 5 μm C18 column (100 Å, 3.9 mm×150 mm) (Waters)

Figure 7:
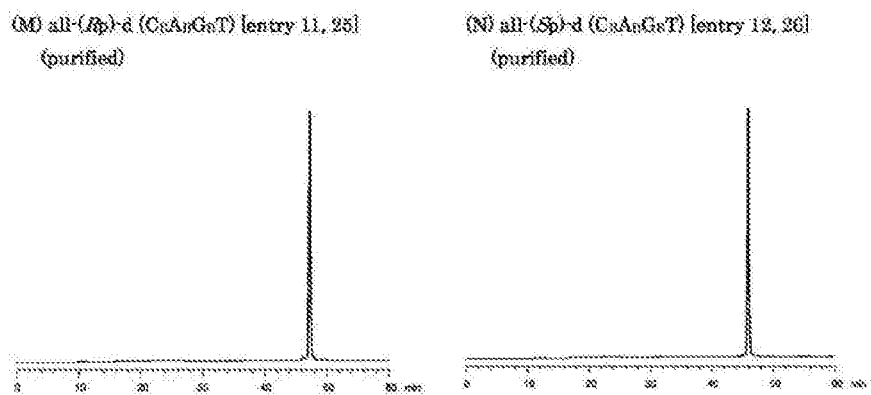
FIG. 7 shows HPLC charts showing results of reverse phase HPLC of (M) a purified product of all-(Rp)-d ($C_BA_BG_BT$) [25] and (N) a purified product of all-(Sp)-d ($C_BA_BG_BT$) [26].

FIG. 7 is HPLC charts showing results of reverse phase HPLC of (K) a purified product of all-(Rp)-d (C$_B$A$_B$G$_B$T) [25] and (L) a purified product of all-(Sp)-d (C$_B$A$_B$G$_B$T) [26].

The measurement conditions of the reverse phase HPLC were as follows.

Gradient cycle: A linear gradient of acetonitrile from 0% to 20% for 60 minutes in a 0.1 M triethylammonium buffer solution (pH 7.0).

Measurement temperature: 30° C.

Flow rate: 0.5 mL/min

Column: μBondasphere 5 μm C18 column (100 Å, 3.9 mm×150 mm) (Waters)

The sequence of the obtained boranophosphate DNA (PB-DNA), the chemical formula [—H$^+$], the theoretical value of a molecular weight (MS), and the measured value by ESI-MS are shown in Table 3, respectively. In addition, in Table 3, description of Rp or Sp indicates whether the absolute configuration of a boranophosphate structure in the oligomer is Sp or Rp. The description of all-(Rp) indicates that the absolute configuration of a boranophosphate structure in the oligomer is all Rp, and the description of all-(Sp) indicates that the absolute configuration of a boranophosphate structure in the oligomer is all Sp, respectively.

TABLE 3

| PB-DNA$^a$ | | Chemical Formula [—H$^+$] | Theoretical value | Measured value |
|---|---|---|---|---|
| (Rp)-24a | (Rp)-T$_B$T | C$_{20}$H$_{29}$BN$_4$O$_{11}$P$^-$ | 542.1705 | 542.1695 |
| (Rp)-24b | (Rp)-dC$_B$T | C$_{19}$H$_{28}$BN$_5$O$_{10}$P$^-$ | 527.1709 | 527.1708 |
| (Rp)-24c | (Rp)-dA$_B$T | C$_{20}$H$_{28}$BN$_7$O$_9$P$^-$ | 551.1821 | 551.1826 |
| (Rp)-24d | (Rp)-dG$_B$T | C$_{20}$H$_{28}$BN$_7$O$_{10}$P$^-$ | 567.1770 | 567.1761 |
| (Sp)-24a | (Sp)-T$_B$T | C$_{20}$H$_{29}$BN$_4$O$_{11}$P$^-$ | 542.1705 | 542.1700 |
| (Sp)-24b | (Sp)-dC$_B$T | C$_{19}$H$_{28}$BN$_5$O$_{10}$P$^-$ | 527.1709 | 527.1710 |
| (Sp)-24c | (Sp)-dA$_B$T | C$_{20}$H$_{28}$BN$_7$O$_9$P$^-$ | 551.1821 | 551.1821 |
| (Sp)-24d | (Sp)-dG$_B$T | C$_{20}$H$_{28}$BN$_7$O$_{10}$P$^-$ | 567.1770 | 567.1763 |
| 25 | all-(Rp)-d(C$_B$A$_B$G$_B$T) | C$_{39}$H$_{57}$B$_3$N$_{15}$O$_{19}$P$_3^-$ | 1166.3549 | 1166.3547 |
| 26 | all-(Sp)-d(C$_B$A$_B$G$_B$T) | C$_{39}$H$_{57}$B$_3$N$_{15}$O$_{19}$P$_3^-$ | 1166.3549 | 1166.3542 |

$^a$"B" represents being bonded by a boranophosphate structure.

<Synthesis 2 of boranophosphate DNA>

According to the following scheme, boranophosphate DNA (PB-DNA) [27] was synthesized. The sequence was all-(Sp)-d(G$_B$T$_B$(A$_B$C$_B$T$_B$)$_3$T). A controlled-pore glass (CPG) as a solid support and a glass filter (10 mm×50 mm) having a cock at the bottom of a reaction vessel were used. The isolated yield was 1.5%.

Other detailed reaction conditions are shown in the following Table 4.

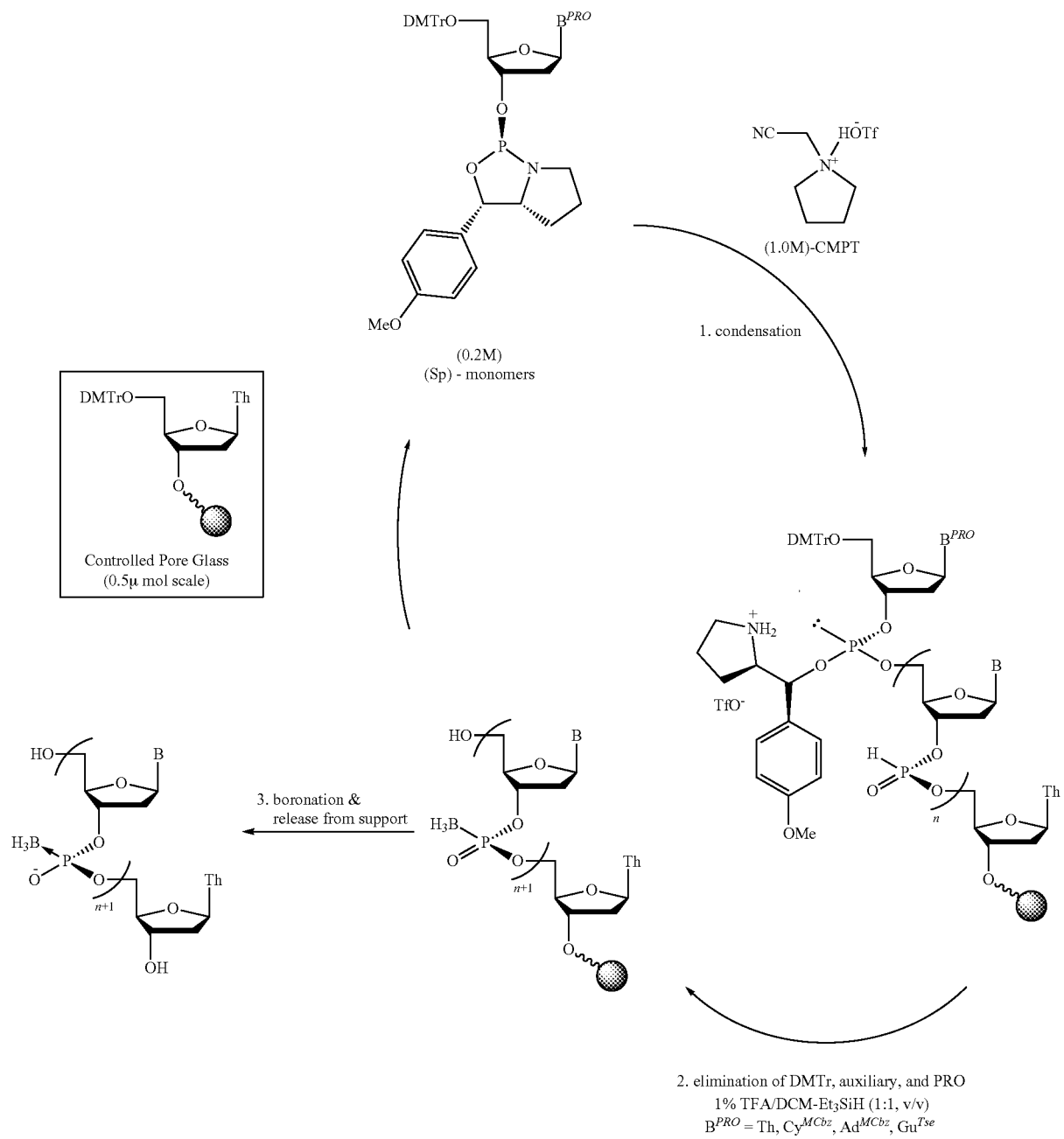

| TABLE 4 | | |
|---|---|---|
| step | manipulation | reagents and solvents | time |
| 1 | detritylation | 1% TFA in DCM | 15 s |
| 2 | wash | (1) DCM (2) CH$_3$CN | — |
| 3 | drying | — | 5 min |
| 4 | condensation | monomer units (0.2M), CMPT (1.0M)/CH$_3$CN | 5 min |
| 5 | wash | CH$_3$CN | — |
| 6 | drying | — | 5 min |
| 7 | wash | (1) DCM (2) CH$_3$CN | — |
| 8 | detritylation and deprotection | 1% TFA in DCM-Et$_3$SiH (1:1, v/v) | 5 min |
| repeat steps 2-8 in order to synthesize the objective sequence | | | |
| 9 | wash | (1) DCM (2) CH$_3$CN | — |
| 10 | boronation | BH$_3$•SMe$_2$-BSA-DMAc (1:1:8, v/v/v) | 15 min |
| 11 | wash | (1) DMAc (2) CH$_3$CN | — |
| 12 | release the oligomer from the CPG | sat.NH$_3$aq-EtOH (3:1, v/v, 50° C.) | 12 h |

In Table 4, monomer units represent Compound 20a-d.

Figure 8:
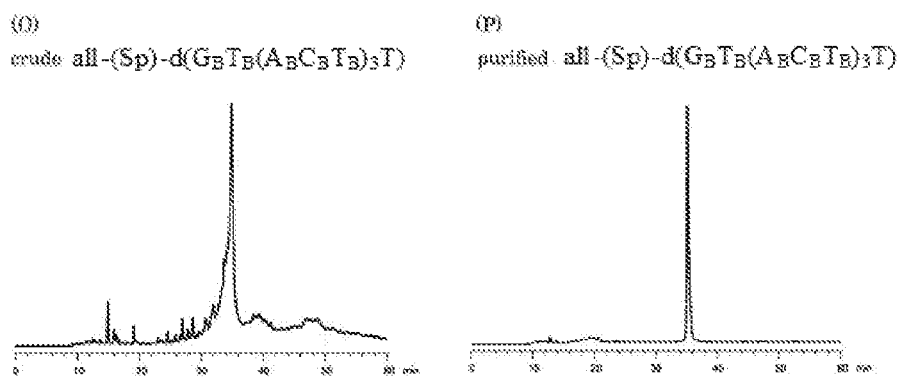
FIG. 8 shows HPLC charts showing results of reverse phase HPLC of (O) a synthesis reaction solution (crude) of all-(Sp)-d($G_BT_B(A_BC_BT_B)_3T$) [27] and (P) a purified product of all-(Sp)-d($G_BT_B(A_BC_BT_B)_3T$) [27].

FIG. 8 is HPLC charts showing results of reverse phase HPLC of (0) a synthesis reaction solution (crude) of all- (Sp)-d($G_BT_B(A_BC_BT_B)_3$T) [27] and (P) a purified product of all-(Sp)-d($G_BT_B(A_BC_BT_B)_3$T) [27].

The measurement conditions of the reverse phase HPLC were as follows.

Gradient cycle: A linear gradient of acetonitrile from 0% to 40% for 60 minutes in a 0.1 M triethylammonium buffer solution (pH 7.0).

Measurement temperature: 30° C.

Flow rate: 0.5 mL/min

Column: µBondasphere 5 µm C18 column (100 Å, 3.9 mm×150 mm) (Waters)

<Synthesis 3 of boranophosphate DNA (Comparative Example)>

According to the following scheme, boranophosphate DNA (PB-DNA) [28, 29] was synthesized. The sequence was all-(Sp)-d($C_BA_BG_BT_B)_2$(CBABGB)T [28] or all-(Rp)-d($C_BA_BG_BT_B)_2$(CBABGB)T [29]. A controlled-pore glass (CPG) as a solid support and a glass filter (10 mm×50 mm) having a cock at the bottom of reaction vessel were used.

Other detailed reaction conditions are shown in the following Table 5.

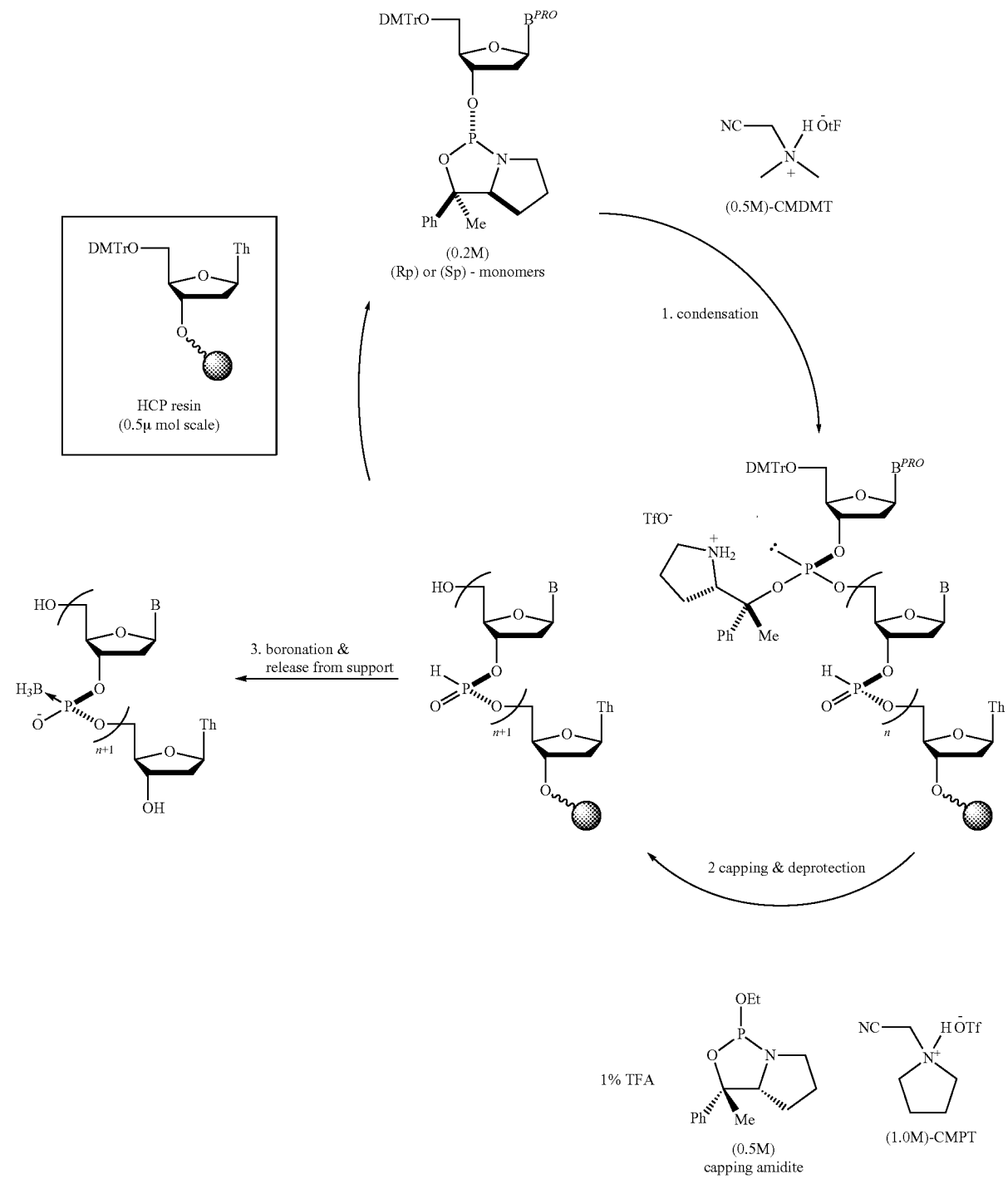

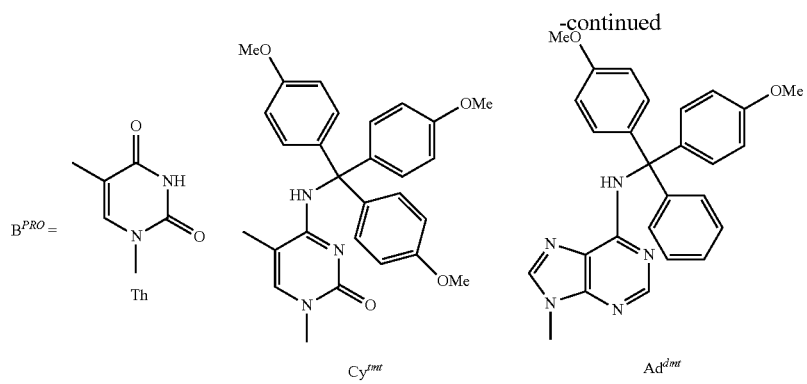

TABLE 5

| step | manipulation | reagents and solvents | time |
|---|---|---|---|
| 1 | detritylation | 1% TFA in DCM | 15 s |
| 2 | wash | (1) DCM (2) CH₃CN | — |
| 3 | drying | — | 10 min |
| 4 | condensation | monomer units (0.2M), CMDMT (0.5M)/CH₃CN-NMP (4:1, v/v) | 5 min |
| 5 | wash | CH₃CN | — |
| 6 | drying | — | 5 min |
| 7 | capping | capping amidite (0.5M), CMPT (1.0M)/CH₃CN | 5 min |
| 8 | wash | (1) DCM (2) CH₃CN | — |
| 9 | detritylation and deprotection | 1% TFA in DCM-Et₃SiH (1:1, v/v) | 15 s |
| | repeat steps 2-9 in order to synthesize the objective sequence | | |
| 10 | wash | (1) DCM (2) CH₃CN | — |
| 11 | boronation | BH₃·SMe₂-BSA-DMAc (1:1:8, v/v/v) | 15 min |
| 12 | wash | (1) DMAc (2) CH₃CN (3) CH₃OH | — |
| 13 | release the oligomer from the HCP resin | sat.NH₃ in CH₂OH (50° C., 0.1 mM) | 12 h |

Figure 9:
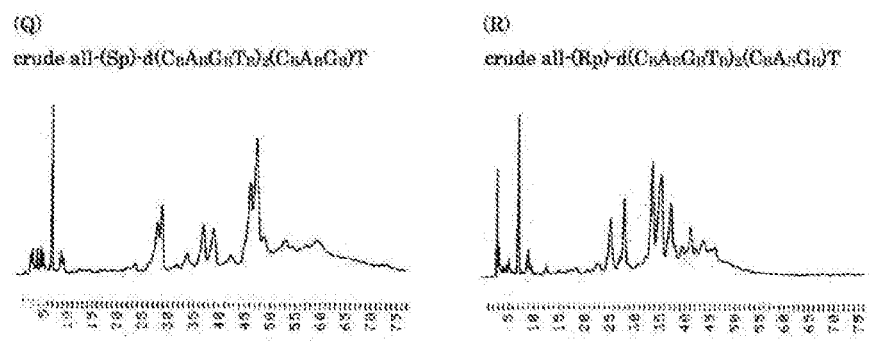
FIG. 9 shows HPLC charts showing results of reverse phase HPLC of (Q) a synthesis reaction solution (crude) of all-(Sp)-d($C_B A_B G_B T_B$)$_2$(CBABGB)T[28] and (R) a synthesis reaction solution (crude) of all-(Rp)-d($C_B A_B G_B T_B$)$_2$(CBABGB)T [29].

FIG. 9 is HPLC charts showing results of reverse phase HPLC of (Q) a synthesis reaction solution (crude) of all-(Sp)-d($C_B A_B G_B T_B$)₂(CBABGB)T[28] and (R) a synthesis reaction solution (crude) of all-(Rp)-d($C_B A_B G_B T_B$)₂(CBABGB)T [29].

The measurement conditions of the reverse phase HPLC were as follows.

Gradient cycle: A linear gradient of acetonitrile from 0% to 40% for 60 minutes in a 0.1 M triethylammonium buffer solution (pH 7.0).

Measurement temperature: 30° C.

Flow rate: 0.5 mL/min

Column: μBondasphere 5 μm C18 column (100 Å, 3.9 mm×150 mm) (Waters)

As can be seen from FIG. 9, according to the Comparative Example, it was impossible to synthesize boranophosphate DNA.

The invention claimed is:

1. A polymerizable compound represented by the following Formula A-1 or Formula A-2:

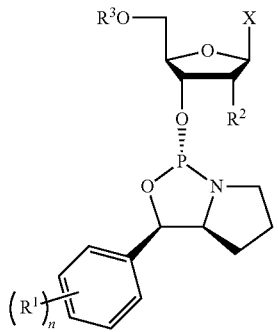

A-1

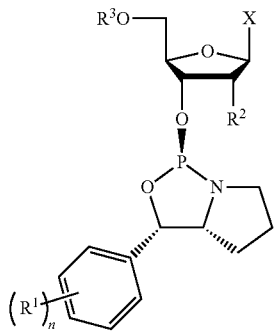

A-2

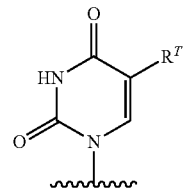

B-1

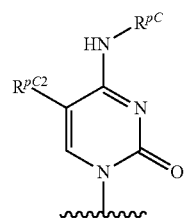

B-2

-continued

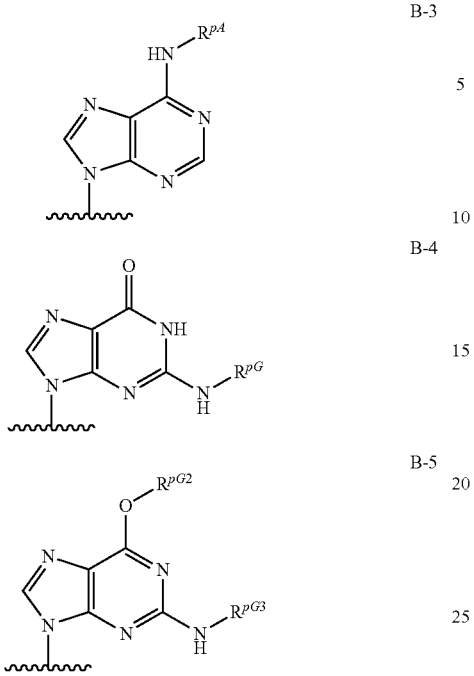

B-3

B-4

B-5 wherein, in Formula A-1 or Formula A-2, $R^1$ represents an electron-donating group selected from the group consisting of an alkoxy group, $-NR^N{}_2$, a hydroxyl group, an aryl group, and an alkyl group, wherein each $R^N$ independently represents a hydrogen atom or an alkyl group having 1 to 10 carbon atoms; n represents an integer from 1 to 5; $R^2$ represents a hydrogen atom, a halogen atom, or $-OR^O$, wherein $R^O$ represents a hydrogen atom, an alkyl group, or a protecting group of a hydroxy group; $R^3$ represents a hydrogen atom or a protecting group of a hydroxy group; and X represents a structure represented by any one of Formula B-1 to Formula B-5, and wherein, in Formula B-1 to Formula B-5, $R^T$ represents a hydrogen atom, an alkyl group, an alkenyl group, or an alkynyl group; each of $R^{pC}$, $R^{pA}$, and $R^{pG}$ represents a protecting group that is removed under an acidic condition; $R^{pC2}$ represents a hydrogen atom or an alkyl group; $R^{pG2}$ represents a protecting group; $R^{pG3}$ represents a protecting group that is removed under an acidic condition, or a hydrogen atom; and ⁓ represents a binding site to a carbon atom at a 1'-position of an adjacent pentose sugar.

2. A compound comprising a structural unit represented by the following Formula T-1 and a structural unit represented by the following Formula D-1 or Formula D-2:

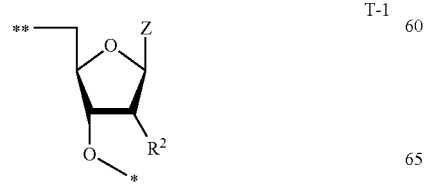

T-1

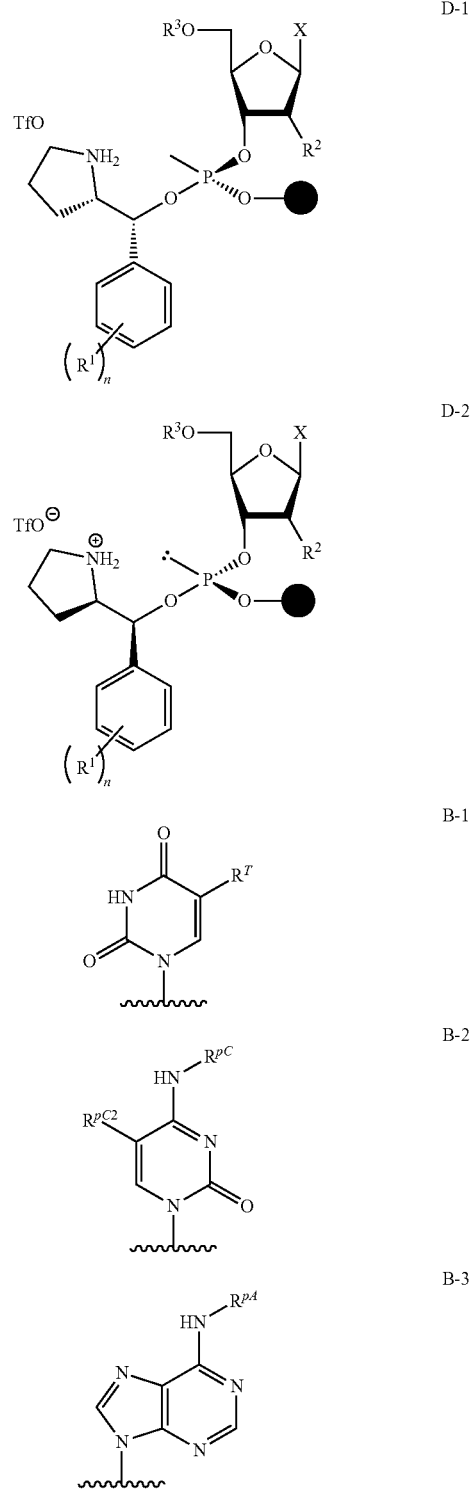

D-1

D-2

B-1

B-2

B-3

B-4

-continued

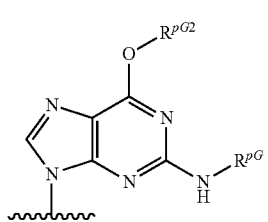
B-5

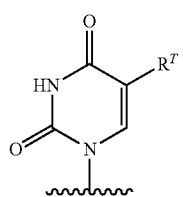
B-6

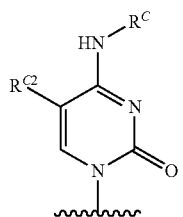
B-7

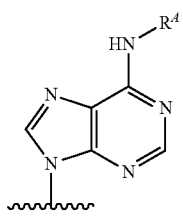
B-8

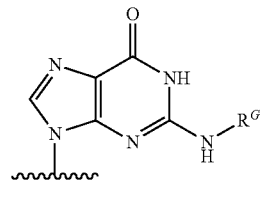
B-9 wherein, in Formula T-1, $R^2$ represents a hydrogen atom, a halogen atom, or $-OR^O$, wherein $R^O$ represents a hydrogen atom, an alkyl group, or a protecting group of a hydroxy group; Z represents a structure represented by any one of Formula B-6 to Formula B-9; and each of * and ** represents a binding site with another structure, wherein, in Formula D-1 or Formula D-2, $R^1$ represents an electron-donating group selected from the group consisting of an alkoxy group, $-NR^N{}_2$, a hydroxyl group, an aryl group, and an alkyl group, wherein each $R^N$ independently represents a hydrogen atom or an alkyl group having 1 to 10 carbon atoms; n represents an integer from 1 to 5; $R^2$ represents a hydrogen atom, a halogen atom, or $-OR^O$, wherein $R^O$ represents a hydrogen atom, an alkyl group, or a protecting group of a hydroxy group; $R^3$ represents a hydrogen atom or a protecting group of a hydroxy group; X represents a structure represented by any one of Formula B-1 to Formula B-5; TfO represents a triflate anion; and ● represents a binding site with another structure, wherein, in Formula B-1 to Formula B-5, $R^T$ represents a hydrogen atom, an alkyl group, an alkenyl group, or an alkynyl group; each of $R^{pC}$, $R^{pA}$, and $R^{pG}$ represents a protecting group that is removed under an acidic condition; $R^{pC2}$ represents a hydrogen atom or an alkyl group; $R^{pG2}$ represents a protecting group; $R^{pG3}$ represents a protecting group that is removed under an acidic condition, or a hydrogen atom; and ~~~ represents a binding site to another structure, and wherein, in Formula B-6 to Formula B-9, $R^T$ represents a hydrogen atom, an alkyl group, an alkenyl group, or an alkynyl group; each of $R^C$, $R^A$, and $R^G$ represents a hydrogen atom; $R^{C2}$ represents a hydrogen atom or an alkyl group; and ~~~ represents a binding site to a carbon atom at a 1'-position of an adjacent pentose sugar.

3. The compound according to claim 2, further comprising one or both structural units represented by the following Formula C-1 or Formula C-2:

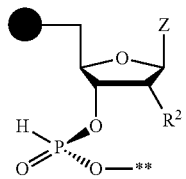
C-1

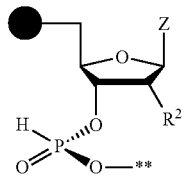
C-2

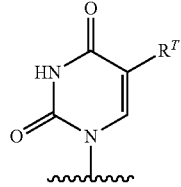
B-6

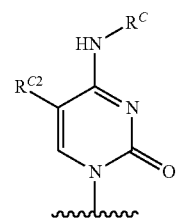
B-7

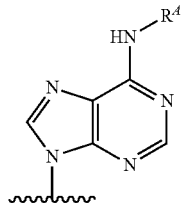
B-8

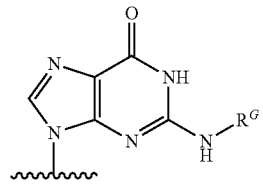

B-9 wherein, in Formula C-1 or Formula C-2, $R^2$ represents a hydrogen atom, a halogen atom, or —$OR^O$, wherein $R^O$ represents a hydrogen atom, an alkyl group, or a protecting group of a hydroxy group; Z represents a structure represented by any one of Formula B-6 to Formula B-9; and each of ** and ● represents a binding site with another structure, and wherein, in Formula B-6 to Formula B-9, $R^T$ represents a hydrogen atom, an alkyl group, an alkenyl group, or an alkynyl group; each of $R^C$, $R^A$, and $R^G$ represents a hydrogen atom; $R^{C2}$ represents a hydrogen atom or an alkyl group; and ⌇ represents a binding site to a carbon atom at a 1'-position of an adjacent pentose sugar.

4. A method of producing a boranophosphate oligomer, comprising condensing the polymerizable compound according to claim 1.

* * * * *